United States Patent [19]

Hayashi et al.

[11] Patent Number: 5,739,008
[45] Date of Patent: Apr. 14, 1998

[54] DNA ENCODING A PROTEIN COMPRISING CALMODULIN-AND ACTIN-BINDING HUMAN CALDESMON PEPTIDE FRAGMENT

[75] Inventors: Ken'ichiro Hayashi, Takatsuki; Takashi Hashida, Otsu; Kiyozo Asada, Shiga-ken; Hirokazu Kotani, Moriyama; Ikunoshin Kato, Uji; Kenji Sobue, 3-5, Higashinakajyo-cho, Ibaraki-shi, Osaka-fu, all of Japan

[73] Assignees: Kenji Sobue, Osaka-Fu; Takara Shuzo Co., Ltd., Kyoto, both of Japan

[21] Appl. No.: 630,349

[22] Filed: Apr. 10, 1996

Related U.S. Application Data

[62] Division of Ser. No. 285,440, Aug. 4, 1994, Pat. No. 5,532,337, which is a continuation of Ser. No. 858,947, Mar. 27, 1992, abandoned.

[30] Foreign Application Priority Data

Mar. 29, 1991 [JP] Japan .................. 3-089106
Dec. 27, 1991 [JP] Japan .................. 3-358040

[51] Int. Cl.$^6$ .................. C12N 15/12; C12N 15/62; C12N 15/63; C12N 5/10
[52] U.S. Cl. .................. 435/69.1; 536/23.4; 536/23.5; 536/24.31; 435/320.1; 435/325; 530/350
[58] Field of Search .................. 536/23.5, 24.31, 536/23.4; 435/320.1, 240.2, 69.1, 69.7, 325; 530/350

[56] References Cited

U.S. PATENT DOCUMENTS 5,532,337 7/1996 Hayashi et al. .................. 530/350

OTHER PUBLICATIONS

Bryan et al., Journal of Biol. Chem., 264, pp. 13873–13879 (Aug. 15, 1989).
Hayashi et al., Biochem. and Biophys. Res. Comm., 164, pp. 503–511 (Oct. 16–1989).
Hayashi et al., J. Biol. Chem., 266, pp. 355–361 (Jan. 5, 1991).
Wang et al., J. Biol. Chem., 266, pp. 9166–9171 (May 15, 1991).
Novy et al., J. Biol. Chem., 266, pp. 16917–16924 (Sep. 5, 1991).
Chemical Abstracts, 115: 249573h (May 31, 1991).
Chemical Abstracts, 116: 122649c (Oct. 28, 1991).
Febs Letters, vol. 218, Jun. 1987, Amsterdam NL pp. 292–294, M.A. Glukhova et al. "Immunoreactive Forms of Caldesmon in Cultivated Human Vascular Smooth Muscle Cells".
Journal of Biological Chemistry (Microfilms) vol. 262, No. 6, Feb. 25, 1987, pp. 2757–2763, T. Fujii et al., "Domain Mapping of Chicken Gizzard Caldesmon".
J. Cell. Biol., 111 (5 part 2), 163A, Abstract No. 894, 1990, New York, US. R.E. Novy et al., "Isolation of a Complementary DNA Encoding a Low M–Gamma Human Caldesmon Isoform" & 30th Annual Meeting of the American Society for Cell Biology San Diego, CA USA, Dec. 9–13, 1990.
Journal of Biological Chemistry, (Microfilms) vol. 266, No. 25, Sep. 5, 1991, pp. 16917–16924 R.E. Novy et al., "Characterization of cDNA Clones Encoding a Human Fibroblast Caldesmon Isoform and Analysis of Caldesmon Expression in Normal and Transformed Cells".
Gene vol. 112, Mar. 15, 1992, Amsterda NL pp. 197–204, M.B. Humphrey et al., "Cloning of cDNAs Encoding Human Caldesmons".
J. Dingus et al. (1986) J. Cell Biol. 102: pp. 1748–1757.
A. Bartegi et al. (1990) J. Biol. Chem. 265: pp. 15231–15238.
J. Sanbrook et al. (1989) Molecular Cloning, Cold Spring Harbor (NY) Press., Ch. 11 & 12 (selected pages).
J. C. Lin et al. (1988) Hybridoma 7: pp. 273–278.
V. M. Riseman et al. (1989) J. Biol. Chem. 264: pp. 2869–2875.
J. H. Collins, (1991) Protein Seq. Data Anal. 4: pp. 29–32.

*Primary Examiner*—Stephen Walsh
*Assistant Examiner*—Michael D. Pak
*Attorney, Agent, or Firm*—Wenderoth, Lind & Ponack

[57] ABSTRACT

Provided are functional peptide fragments of human caldesmon having calmodulin and actin-binding activity, the amino acid sequences and nucleic acid sequences therefor.

12 Claims, 2 Drawing Sheets

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
    ( A ) LENGTH: 116 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:1:

```
Arg Leu Glu Gln Tyr Thr Ser Ala Ile Glu Gly Thr Lys Ser Ala
 1               5                  10                  15

Lys Pro Thr Lys Pro Ala Ala Ser Asp Leu Pro Val Pro Ala Glu
                20                  25                  30

Gly Val Arg Asn Ile Lys Ser Met Trp Glu Lys Gly Asn Val Phe
                35                  40                  45

Ser Ser Pro Thr Ala Ala Gly Thr Pro Asn Lys Glu Thr Ala Gly
                50                  55                  60

Leu Lys Val Gly Val Ser Ser Arg Ile Asn Glu Trp Leu Thr Lys
                65                  70                  75

Thr Pro Asp Gly Asn Lys Ser Pro Ala Pro Lys Pro Ser Asp Leu
                80                  85                  90

Arg Pro Gly Asp Val Ser Ser Lys Arg Asn Leu Trp Glu Lys Gln
                95                 100                 105

Ser Val Asp Lys Val Thr Ser Pro Thr Lys Val
               110                 115
```

( 2 ) INFORMATION FOR SEQ ID NO:2:

( i ) SEQUENCE CHARACTERISTICS:
    ( A ) LENGTH: 118 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:2:

```
Met Ala Arg Leu Glu Gln Tyr Thr Ser Ala Ile Glu Gly Thr Lys
 1               5                  10                  15

Ser Ala Lys Pro Thr Lys Pro Ala Ala Ser Asp Leu Pro Val Pro
                20                  25                  30

Ala Glu Gly Val Arg Asn Ile Lys Ser Met Trp Glu Lys Gly Asn
                35                  40                  45

Val Phe Ser Ser Pro Thr Ala Ala Gly Thr Pro Asn Lys Glu Thr
                50                  55                  60

Ala Gly Leu Lys Val Gly Val Ser Ser Arg Ile Asn Glu Trp Leu
                65                  70                  75

Thr Lys Thr Pro Asp Gly Asn Lys Ser Pro Ala Pro Lys Pro Ser
                80                  85                  90

Asp Leu Arg Pro Gly Asp Val Ser Ser Lys Arg Asn Leu Trp Glu
                95                 100                 105

Lys Gln Ser Val Asp Lys Val Thr Ser Pro Thr Lys Val
               110                 115
```

( 2 ) INFORMATION FOR SEQ ID NO:3:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Met Ala Ile Glu Gly Arg Arg Leu Glu Gln Tyr Thr Ser Ala Ile
 1               5                  10                  15

Glu Gly Thr Lys Ser Ala Lys Pro Thr Lys Pro Ala Ala Ser Asp
                20                  25                  30

Leu Pro Val Pro Ala Glu Gly Val Arg Asn Ile Lys Ser Met Trp
                35                  40                  45

Glu Lys Gly Asn Val Phe Ser Ser Pro Thr Ala Ala Gly Thr Pro
                50                  55                  60

Asn Lys Glu Thr Ala Gly Leu Lys Val Gly Val Ser Ser Arg Ile
                65                  70                  75

Asn Glu Trp Leu Thr Lys Thr Pro Asp Gly Asn Lys Ser Pro Ala
                80                  85                  90

Pro Lys Pro Ser Asp Leu Arg Pro Gly Asp Val Ser Ser Lys Arg
                95                 100                 105

Asn Leu Trp Glu Lys Gln Ser Val Asp Lys Val Thr Ser Pro Thr
               110                 115                 120

Lys Val
```

( 2 ) INFORMATION FOR SEQ ID NO:4:

( i ) SEQUENCE CHARACTERISTICS:
        ( A ) LENGTH: 312 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Met Asp Arg Lys Lys Gly Phe Thr Glu Val Lys Ser Gln Asn Gly
 1               5                  10                  15

Glu Phe Met Thr His Lys Leu Lys His Thr Glu Asn Thr Phe Ser
                20                  25                  30

Arg Pro Gly Gly Arg Ala Ser Val Asp Thr Lys Glu Ala Glu Gly
                35                  40                  45

Ala Pro Gln Val Glu Ala Gly Lys Arg Leu Glu Glu Leu Arg Arg
                50                  55                  60

Arg Arg Gly Glu Thr Glu Ser Glu Glu Phe Glu Lys Leu Lys Gln
                65                  70                  75

Lys Gln Gln Glu Ala Ala Leu Glu Leu Glu Glu Leu Lys Lys Lys
                80                  85                  90

Arg Glu Glu Arg Arg Lys Val Leu Glu Glu Glu Glu Gln Arg Arg
                95                 100                 105

Lys Gln Glu Glu Ala Asp Arg Lys Leu Arg Glu Glu Glu Glu Lys
               110                 115                 120

Arg Arg Leu Lys Glu Glu Ile Glu Arg Arg Arg Ala Glu Ala Ala
               125                 130                 135
```

| Glu | Lys | Arg | Gln | Lys<br>140 | Met | Pro | Glu | Asp | Gly<br>145 | Leu | Ser | Asp | Asp | Lys<br>150 |
| --- | --- | --- | --- | --- | --- | --- | --- | --- | --- | --- | --- | --- | --- | --- |
| Lys | Pro | Phe | Lys | Cys<br>155 | Phe | Thr | Pro | Lys | Gly<br>160 | Ser | Ser | Leu | Lys | Ile<br>165 |
| Glu | Glu | Arg | Ala | Glu<br>170 | Phe | Leu | Asn | Lys | Ser<br>175 | Val | Gln | Lys | Ser | Ser<br>180 |
| Gly | Val | Lys | Ser | Thr<br>185 | His | Gln | Ala | Ala | Ile<br>190 | Val | Ser | Lys | Ile | Asp<br>195 |
| Ser | Arg | Leu | Glu | Gln<br>200 | Tyr | Thr | Ser | Ala | Ile<br>205 | Glu | Gly | Thr | Lys | Ser<br>210 |
| Ala | Lys | Pro | Thr | Lys<br>215 | Pro | Ala | Ala | Ser | Asp<br>220 | Leu | Pro | Val | Pro | Ala<br>225 |
| Glu | Gly | Val | Arg | Asn<br>230 | Ile | Lys | Ser | Met | Trp<br>235 | Glu | Lys | Gly | Asn | Val<br>240 |
| Phe | Ser | Ser | Pro | Thr<br>245 | Ala | Ala | Gly | Thr | Pro<br>250 | Asn | Lys | Glu | Thr | Ala<br>255 |
| Gly | Leu | Lys | Val | Gly<br>260 | Val | Ser | Ser | Arg | Ile<br>265 | Asn | Glu | Trp | Leu | Thr<br>270 |
| Lys | Thr | Pro | Asp | Gly<br>275 | Asn | Lys | Ser | Pro | Ala<br>280 | Pro | Lys | Pro | Ser | Asp<br>285 |
| Leu | Arg | Pro | Gly | Asp<br>290 | Val | Ser | Ser | Lys | Arg<br>295 | Asn | Leu | Trp | Glu | Lys<br>300 |
| Gln | Ser | Val | Asp | Lys<br>305 | Val | Thr | Ser | Pro | Thr<br>310 | Lys | Val | | | |

(2) INFORMATION FOR SEQ ID NO:5:

(i) SEQUENCE CHARACTERISTICS:
      (A) LENGTH: 532 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:5:

| Met<br>1 | Leu | Gly | Gly | Ser<br>5 | Gly | Ser | His | Gly | Arg<br>10 | Arg | Ser | Leu | Ala | Ala<br>15 |
| --- | --- | --- | --- | --- | --- | --- | --- | --- | --- | --- | --- | --- | --- | --- |
| Leu | Ser | Gln | Ile | Ala<br>20 | Tyr | Gln | Arg | Asn | Asp<br>25 | Asp | Asp | Glu | Glu | Glu<br>30 |
| Ala | Ala | Arg | Glu | Arg<br>35 | Arg | Arg | Arg | Ala | Arg<br>40 | Gln | Glu | Arg | Leu | Arg<br>45 |
| Gln | Lys | Gln | Glu | Glu<br>50 | Glu | Ser | Leu | Gly | Gln<br>55 | Val | Thr | Asp | Gln | Val<br>60 |
| Glu | Val | Asn | Ala | Gln<br>65 | Asn | Ser | Val | Pro | Asp<br>70 | Glu | Glu | Ala | Lys | Thr<br>75 |
| Thr | Thr | Thr | Asn | Thr<br>80 | Gln | Val | Glu | Gly | Asp<br>85 | Asp | Glu | Ala | Ala | Phe<br>90 |
| Leu | Glu | Arg | Leu | Ala<br>95 | Arg | Arg | Glu | Glu | Arg<br>100 | Arg | Gln | Lys | Arg | Leu<br>105 |
| Gln | Glu | Ala | Leu | Glu<br>110 | Arg | Gln | Lys | Glu | Phe<br>115 | Asp | Pro | Thr | Ile | Thr<br>120 |
| Asp | Ala | Ser | Leu | Ser<br>125 | Leu | Pro | Ser | Arg | Arg<br>130 | Met | Gln | Asn | Asp | Thr<br>135 |
| Ala | Glu | Asn | Glu | Thr<br>140 | Thr | Glu | Lys | Glu | Glu<br>145 | Lys | Ser | Glu | Ser | Arg<br>150 |
| Gln | Glu | Arg | Tyr | Glu | Ile | Glu | Glu | Thr | Glu | Thr | Val | Thr | Lys | Ser |

|     |     |     |     | 155 |     |     |     |     | 160 |     |     |     |     | 165 |
| --- | --- | --- | --- | --- | --- | --- | --- | --- | --- | --- | --- | --- | --- | --- |
| Tyr | Gln | Lys | Asn | Asp | Trp | Arg | Asp | Ala | Glu | Glu | Asn | Lys | Lys | Glu |
|     |     |     |     | 170 |     |     |     |     | 175 |     |     |     |     | 180 |
| Asp | Lys | Glu | Lys | Glu | Glu | Glu | Glu | Glu | Glu | Lys | Pro | Lys | Arg | Gly |
|     |     |     |     | 185 |     |     |     |     | 190 |     |     |     |     | 195 |
| Ser | Ile | Gly | Glu | Asn | Gln | Ile | Lys | Asp | Glu | Lys | Ile | Lys | Lys | Asp |
|     |     |     |     | 200 |     |     |     |     | 205 |     |     |     |     | 210 |
| Lys | Glu | Pro | Lys | Glu | Glu | Val | Lys | Ser | Phe | Met | Asp | Arg | Lys | Lys |
|     |     |     |     | 215 |     |     |     |     | 220 |     |     |     |     | 225 |
| Gly | Phe | Thr | Glu | Val | Lys | Ser | Gln | Asn | Gly | Glu | Phe | Met | Thr | His |
|     |     |     |     | 230 |     |     |     |     | 235 |     |     |     |     | 240 |
| Lys | Leu | Lys | His | Thr | Glu | Asn | Thr | Phe | Ser | Arg | Pro | Gly | Gly | Arg |
|     |     |     |     | 245 |     |     |     |     | 250 |     |     |     |     | 255 |
| Ala | Ser | Val | Asp | Thr | Lys | Glu | Ala | Glu | Gly | Ala | Pro | Gln | Val | Glu |
|     |     |     |     | 260 |     |     |     |     | 265 |     |     |     |     | 270 |
| Ala | Gly | Lys | Arg | Leu | Glu | Glu | Leu | Arg | Arg | Arg | Arg | Gly | Glu | Thr |
|     |     |     |     | 275 |     |     |     |     | 280 |     |     |     |     | 285 |
| Glu | Ser | Glu | Glu | Phe | Glu | Lys | Leu | Lys | Gln | Lys | Gln | Gln | Glu | Ala |
|     |     |     |     | 290 |     |     |     |     | 295 |     |     |     |     | 300 |
| Ala | Leu | Glu | Leu | Glu | Glu | Leu | Lys | Lys | Lys | Arg | Glu | Glu | Arg | Arg |
|     |     |     |     | 305 |     |     |     |     | 310 |     |     |     |     | 315 |
| Lys | Val | Leu | Glu | Glu | Glu | Glu | Gln | Arg | Arg | Lys | Gln | Glu | Glu | Ala |
|     |     |     |     | 320 |     |     |     |     | 325 |     |     |     |     | 330 |
| Asp | Arg | Lys | Leu | Arg | Glu | Glu | Glu | Glu | Lys | Arg | Arg | Leu | Lys | Glu |
|     |     |     |     | 335 |     |     |     |     | 340 |     |     |     |     | 345 |
| Glu | Ile | Glu | Arg | Arg | Arg | Ala | Glu | Ala | Ala | Glu | Lys | Arg | Gln | Lys |
|     |     |     |     | 350 |     |     |     |     | 355 |     |     |     |     | 360 |
| Met | Pro | Glu | Asp | Gly | Leu | Ser | Asp | Asp | Lys | Lys | Pro | Phe | Lys | Cys |
|     |     |     |     | 365 |     |     |     |     | 370 |     |     |     |     | 375 |
| Phe | Thr | Pro | Lys | Gly | Ser | Ser | Leu | Lys | Ile | Glu | Glu | Arg | Ala | Glu |
|     |     |     |     | 380 |     |     |     |     | 385 |     |     |     |     | 390 |
| Phe | Leu | Asn | Lys | Ser | Val | Gln | Lys | Ser | Ser | Gly | Val | Lys | Ser | Thr |
|     |     |     |     | 395 |     |     |     |     | 400 |     |     |     |     | 405 |
| His | Gln | Ala | Ala | Ile | Val | Ser | Lys | Ile | Asp | Ser | Arg | Leu | Glu | Gln |
|     |     |     |     | 410 |     |     |     |     | 415 |     |     |     |     | 420 |
| Tyr | Thr | Ser | Ala | Ile | Glu | Gly | Thr | Lys | Ser | Ala | Lys | Pro | Thr | Lys |
|     |     |     |     | 425 |     |     |     |     | 430 |     |     |     |     | 435 |
| Pro | Ala | Ala | Ser | Asp | Leu | Pro | Val | Pro | Ala | Glu | Gly | Val | Arg | Asn |
|     |     |     |     | 440 |     |     |     |     | 445 |     |     |     |     | 450 |
| Ile | Lys | Ser | Met | Trp | Glu | Lys | Gly | Asn | Val | Phe | Ser | Ser | Pro | Thr |
|     |     |     |     | 455 |     |     |     |     | 460 |     |     |     |     | 465 |
| Ala | Ala | Gly | Thr | Pro | Asn | Lys | Glu | Thr | Ala | Gly | Leu | Lys | Val | Gly |
|     |     |     |     | 470 |     |     |     |     | 475 |     |     |     |     | 480 |
| Val | Ser | Ser | Arg | Ile | Asn | Glu | Trp | Leu | Thr | Lys | Thr | Pro | Asp | Gly |
|     |     |     |     | 485 |     |     |     |     | 490 |     |     |     |     | 495 |
| Asn | Lys | Ser | Pro | Ala | Pro | Lys | Pro | Ser | Asp | Leu | Arg | Pro | Gly | Asp |
|     |     |     |     | 500 |     |     |     |     | 505 |     |     |     |     | 510 |
| Val | Ser | Ser | Lys | Arg | Asn | Leu | Trp | Glu | Lys | Gln | Ser | Val | Asp | Lys |
|     |     |     |     | 515 |     |     |     |     | 520 |     |     |     |     | 525 |
| Val | Thr | Ser | Pro | Thr | Lys | Val |     |     |     |     |     |     |     |     |
|     |     |     |     | 530 |     |     |     |     |     |     |     |     |     |     |

( 2 ) INFORMATION FOR SEQ ID NO:6:

( i ) SEQUENCE CHARACTERISTICS:
  ( A ) LENGTH: 558 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:6:

```
Met Leu Gly Gly Ser Gly Ser His Gly Arg Arg Ser Leu Ala Ala
 1               5                  10                  15

Leu Ser Gln Ile Ala Tyr Gln Arg Asn Asp Asp Glu Glu Glu
                20                  25                  30

Ala Ala Arg Glu Arg Arg Arg Arg Ala Arg Gln Glu Arg Leu Arg
                35                  40                  45

Gln Lys Gln Glu Glu Glu Ser Leu Gly Gln Val Thr Asp Gln Val
                50                  55                  60

Glu Val Asn Ala Gln Asn Ser Val Pro Asp Glu Glu Ala Lys Thr
                65                  70                  75

Thr Thr Thr Asn Thr Gln Val Glu Gly Asp Asp Glu Ala Ala Phe
                80                  85                  90

Leu Glu Arg Leu Ala Arg Arg Glu Glu Arg Arg Gln Lys Arg Leu
                95                  100                 105

Gln Glu Ala Leu Glu Arg Gln Lys Glu Phe Asp Pro Thr Ile Thr
                110                 115                 120

Asp Ala Ser Leu Ser Leu Pro Ser Arg Arg Met Gln Asn Asp Thr
                125                 130                 135

Ala Glu Asn Glu Thr Thr Glu Lys Glu Glu Lys Ser Glu Ser Arg
                140                 145                 150

Gln Glu Arg Tyr Glu Ile Glu Glu Thr Glu Thr Val Thr Lys Ser
                155                 160                 165

Tyr Gln Lys Asn Asp Trp Arg Asp Ala Glu Glu Asn Lys Lys Glu
                170                 175                 180

Asp Lys Glu Lys Glu Glu Glu Glu Glu Glu Lys Pro Lys Arg Gly
                185                 190                 195

Ser Ile Gly Glu Asn Gln Gly Glu Glu Lys Gly Thr Lys Val Gln
                200                 205                 210

Ala Lys Arg Glu Lys Leu Gln Glu Asp Lys Pro Thr Phe Lys Lys
                215                 220                 225

Glu Glu Ile Lys Asp Glu Lys Ile Lys Lys Asp Lys Glu Pro Lys
                230                 235                 240

Glu Glu Val Lys Ser Phe Met Asp Arg Lys Lys Gly Phe Thr Glu
                245                 250                 255

Val Lys Ser Gln Asn Gly Glu Phe Met Thr His Lys Leu Lys His
                260                 265                 270

Thr Glu Asn Thr Phe Ser Arg Pro Gly Gly Arg Ala Ser Val Asp
                275                 280                 285

Thr Lys Glu Ala Glu Gly Ala Pro Gln Val Glu Ala Gly Lys Arg
                290                 295                 300

Leu Glu Glu Leu Arg Arg Arg Arg Gly Glu Thr Glu Ser Glu Glu
                305                 310                 315

Phe Glu Lys Leu Lys Gln Lys Gln Glu Ala Ala Leu Glu Leu
                320                 325                 330

Glu Glu Leu Lys Lys Lys Arg Glu Glu Arg Arg Lys Val Leu Glu
                335                 340                 345

Glu Glu Glu Gln Arg Arg Lys Gln Glu Glu Ala Asp Arg Lys Leu
```

-continued

| | | | | 350 | | | | | 355 | | | | 360 |
|---|---|---|---|---|---|---|---|---|---|---|---|---|---|
| Arg | Glu | Glu | Glu | Glu | Lys | Arg | Arg | Leu | Lys | Glu | Glu | Ile | Glu | Arg |
| | | | | 365 | | | | | 370 | | | | 375 |
| Arg | Arg | Ala | Glu | Ala | Ala | Glu | Lys | Arg | Gln | Lys | Met | Pro | Glu | Asp |
| | | | | 380 | | | | | 385 | | | | 390 |
| Gly | Leu | Ser | Asp | Asp | Lys | Lys | Pro | Phe | Lys | Cys | Phe | Thr | Pro | Lys |
| | | | | 395 | | | | | 400 | | | | 405 |
| Gly | Ser | Ser | Leu | Lys | Ile | Glu | Glu | Arg | Ala | Glu | Phe | Leu | Asn | Lys |
| | | | | 410 | | | | | 415 | | | | 420 |
| Ser | Val | Gln | Lys | Ser | Ser | Gly | Val | Lys | Ser | Thr | His | Gln | Ala | Ala |
| | | | | 425 | | | | | 430 | | | | 435 |
| Ile | Val | Ser | Lys | Ile | Asp | Ser | Arg | Leu | Glu | Gln | Tyr | Thr | Ser | Ala |
| | | | | 440 | | | | | 445 | | | | 450 |
| Ile | Glu | Gly | Thr | Lys | Ser | Ala | Lys | Pro | Thr | Lys | Pro | Ala | Ala | Ser |
| | | | | 455 | | | | | 460 | | | | 465 |
| Asp | Leu | Pro | Val | Pro | Ala | Glu | Gly | Val | Arg | Asn | Ile | Lys | Ser | Met |
| | | | | 470 | | | | | 475 | | | | 480 |
| Trp | Glu | Lys | Gly | Asn | Val | Phe | Ser | Ser | Pro | Thr | Ala | Ala | Gly | Thr |
| | | | | 485 | | | | | 490 | | | | 495 |
| Pro | Asn | Lys | Glu | Thr | Ala | Gly | Leu | Lys | Val | Gly | Val | Ser | Ser | Arg |
| | | | | 500 | | | | | 505 | | | | 510 |
| Ile | Asn | Glu | Trp | Leu | Thr | Lys | Thr | Pro | Asp | Gly | Asn | Lys | Ser | Pro |
| | | | | 515 | | | | | 520 | | | | 525 |
| Ala | Pro | Lys | Pro | Ser | Asp | Leu | Arg | Pro | Gly | Asp | Val | Ser | Ser | Lys |
| | | | | 530 | | | | | 535 | | | | 540 |
| Arg | Asn | Leu | Trp | Glu | Lys | Gln | Ser | Val | Asp | Lys | Val | Thr | Ser | Pro |
| | | | | 545 | | | | | 550 | | | | 555 |
| Thr | Lys | Val | | | | | | | | | | | | |

( 2 ) INFORMATION FOR SEQ ID NO:7:

( i ) SEQUENCE CHARACTERISTICS:
        ( A ) LENGTH: 348 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE: Human ( v i i ) IMMEDIATE SOURCE: Hela Cell ( x i ) SEQUENCE DESCRIPTION: SEQ ID NO:7:

| | | | | | |
|---|---|---|---|---|---|
| AGACTGGAGC | AGTATACCAG | TGCAATTGAG | GGAACAAAAA | GCGCAAAACC | TACAAAGCCG | 60 |
| GCAGCCTCGG | ATCTTCCTGT | TCCTGCTGAA | GGTGTACGCA | ACATCAAGAG | TATGTGGGAG | 120 |
| AAAGGGAATG | TGTTTTCATC | CCCCACTGCA | GCAGGCACAC | CAAATAAGGA | AACTGCTGGC | 180 |
| TTGAAGGTAG | GGGTTTCTAG | CCGTATCAAT | GAATGGCTAA | CTAAAACCCC | AGATGGAAAC | 240 |
| AAGTCACCTG | CTCCCAAACC | TTCTGACTTG | AGACCAGGAG | ACGTATCCAG | CAAGCGGAAC | 300 |
| CTCTGGGAAA | AGCAATCTGT | GGATAAGGTC | ACTTCCCCCA | CTAAGGTT | | 348 |

( 2 ) INFORMATION FOR SEQ ID NO:8:

( i ) SEQUENCE CHARACTERISTICS:
        ( A ) LENGTH: 357 base pairs
        ( B ) TYPE: nucleic acid
        ( C ) STRANDEDNESS: double
        ( D ) TOPOLOGY: linear (i i) MOLECULE TYPE: cDNA to mRNA (v i) ORIGINAL SOURCE: Human (v i i) IMMEDIATE SOURCE: Hela Cell (x i) SEQUENCE DESCRIPTION: SEQ ID NO:8:

| | | | | | | |
|---|---|---|---|---|---|---|
| ATGGCCAGAC | TGGAGCAGTA | TACCAGTGCA | ATTGAGGGAA | CAAAAAGCGC | AAAACCTACA | 60 |
| AAGCCGGCAG | CCTCGGATCT | TCCTGTTCCT | GCTGAAGGTG | TACGCAACAT | CAAGAGTATG | 120 |
| TGGGAGAAAG | GGAATGTGTT | TTCATCCCCC | ACTGCAGCAG | GCACACCAAA | TAAGGAAACT | 180 |
| GCTGGCTTGA | AGGTAGGGGT | TTCTAGCCGT | ATCAATGAAT | GGCTAACTAA | AACCCCAGAT | 240 |
| GGAAACAAGT | CACCTGCTCC | CAAACCTTCT | GACTTGAGAC | CAGGAGACGT | ATCCAGCAAG | 300 |
| CGGAACCTCT | GGGAAAAGCA | ATCTGTGGAT | AAGGTCACTT | CCCCCACTAA | GGTTTGA | 357 |

(2) INFORMATION FOR SEQ ID NO:9:

(i) SEQUENCE CHARACTERISTICS:
    (A) LENGTH: 369 base pairs
    (B) TYPE: nucleic acid
    (C) STRANDEDNESS: double
    (D) TOPOLOGY: linear (i i) MOLECULE TYPE: cDNA to mRNA (v i) ORIGINAL SOURCE: Human (v i i) IMMEDIATE SOURCE: Hela Cell (x i) SEQUENCE DESCRIPTION: SEQ ID NO:9:

| | | | | | | |
|---|---|---|---|---|---|---|
| ATGGCCATCG | AGGGTAGGAG | ACTGGAGCAG | TATACCAGTG | CAATTGAGGG | AACAAAAAGC | 60 |
| GCAAAACCTA | CAAAGCCGGC | AGCCTCGGAT | CTTCCTGTTC | CTGCTGAAGG | TGTACGCAAC | 120 |
| ATCAAGAGTA | TGTGGGAGAA | AGGGAATGTG | TTTTCATCCC | CCACTGCAGC | AGGCACACCA | 180 |
| AATAAGGAAA | CTGCTGGCTT | GAAGGTAGGG | GTTTCTAGCC | GTATCAATGA | ATGGCTAACT | 240 |
| AAAACCCCAG | ATGGAAACAA | GTCACCTGCT | CCCAAACCTT | CTGACTTGAG | ACCAGGAGAC | 300 |
| GTATCCAGCA | AGCGGAACCT | CTGGGAAAAG | CAATCTGTGG | ATAAGGTCAC | TTCCCCCACT | 360 |
| AAGGTTTGA | | | | | | 369 |

(2) INFORMATION FOR SEQ ID NO:10:

(i) SEQUENCE CHARACTERISTICS:
    (A) LENGTH: 939 base pairs
    (B) TYPE: nucleic acid
    (C) STRANDEDNESS: double
    (D) TOPOLOGY: linear (i i) MOLECULE TYPE: cDNA to mRNA (v i) ORIGINAL SOURCE: Human (v i i) IMMEDIATE SOURCE: Hela Cell (x i) SEQUENCE DESCRIPTION: SEQ ID NO:10:

| | | | | | | |
|---|---|---|---|---|---|---|
| ATGGATCGAA | AGAAGGGATT | TACAGAAGTT | AAGTCGCAGA | ATGGAGAATT | CATGACCCAC | 60 |
| AAACTTAAAC | ATACTGAGAA | TACTTTCAGC | CGCCCTGGAG | GGAGGGCCAG | CGTGGACACC | 120 |
| AAGGAGGCTG | AGGGCGCCCC | CCAGGTGGAA | GCCGGCAAAA | GGCTGGAGGA | GCTTCGTCGT | 180 |
| CGTCGCGGGG | AGACCGAGAG | CGAAGAGTTC | GAGAAGCTCA | AACAGAAGCA | GCAGGAGGCG | 240 |
| GCTTTGGAGC | TGGAGGAACT | CAAGAAAAAG | AGGGAGGAGA | GAAGGAAGGT | CCTGGAGGAG | 300 |
| GAAGAGCAGA | GGAGGAAGCA | GGAGGAAGCC | GATCGAAAAC | TCAGAGAGGA | GGAAGAGAAG | 360 |

```
AGGAGGCTAA  AGGAAGAGAT  TGAAAGGCGA  AGAGCAGAAG  CTGCTGAGAA  ACGCCAGAAG    420

ATGCCAGAAG  ATGGCTTGTC  AGATGACAAG  AAACCATTCA  AGTGTTTCAC  TCCTAAAGGT    480

TCATCTCTCA  AGATAGAAGA  GCGAGCAGAA  TTTTTGAATA  AGTCTGTGCA  GAAAAGCAGT    540

GGTGTCAAAT  CGACCCATCA  AGCAGCAATA  GTCTCCAAGA  TTGACAGCAG  ACTGGAGCAG    600

TATACCAGTG  CAATTGAGGG  AACAAAAAGC  GCAAAACCTA  CAAAGCCGGC  AGCCTCGGAT    660

CTTCCTGTTC  CTGCTGAAGG  TGTACGCAAC  ATCAAGAGTA  TGTGGGAGAA  AGGGAATGTG    720

TTTTCATCCC  CCACTGCAGC  AGGCACACCA  AATAAGGAAA  CTGCTGGCTT  GAAGGTAGGG    780

GTTTCTAGCC  GTATCAATGA  ATGGCTAACT  AAAACCCCAG  ATGGAAACAA  GTCACCTGCT    840

CCCAAACCTT  CTGACTTGAG  ACCAGGAGAC  GTATCCAGCA  AGCGGAACCT  CTGGGAAAAG    900

CAATCTGTGG  ATAAGGTCAC  TTCCCCCACT  AAGGTTTGA                              939
```

( 2 ) INFORMATION FOR SEQ ID NO:11:

( i ) SEQUENCE CHARACTERISTICS:
        ( A ) LENGTH: 1599 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE: Human ( v i i ) IMMEDIATE SOURCE: Hela Cell ( x i ) SEQUENCE DESCRIPTION: SEQ ID NO:11:

```
ATGCTGGGTG  GATCCGGATC  GCATGGAAGA  CGCAGCCTGG  CCGCGCTCTC  CCAAATCGCC     60

TACCAGAGGA  ATGACGATGA  TGAAGAGGAG  GCAGCCCGGG  AACGGCGCCG  CCGAGCCCGA    120

CAGGAACGGC  TGCGGCAGAA  GCAGGAGGAA  GAATCCTTGG  GACAGGTGAC  CGACCAGGTG    180

GAGGTGAATG  CCCAGAACAG  TGTGCCTGAC  GAGGAGGCCA  AGACAACCAC  CACAAACACT    240

CAAGTGGAAG  GGGATGATGA  GGCCGCATTC  CTGGAGCGCC  TGGCTCGGCG  TGAGGAAAGA    300

CGCCAAAAAC  GCCTTCAGGA  GGCTCTGGAG  CGGCAGAAGG  AGTTCGACCC  AACAATAACA    360

GATGCAAGTC  TGTCGCTCCC  AAGCAGAAGA  ATGCAAAATG  ACACAGCAGA  AAATGAAACT    420

ACCGAGAAGG  AAGAAAAAAG  TGAAAGTCGC  CAAGAAAGAT  ACGAGATAGA  GGAAACAGAA    480

ACAGTCACCA  AGTCCTACCA  GAAGAATGAT  TGGAGGGATG  CTGAAGAAAA  CAAGAAAGAA    540

GACAAGGAAA  AGGAGGAGGA  GGAAGAGGAG  AAGCCAAAGC  GAGGGAGCAT  GGAGAAAAT    600

CAGATCAAAG  ATGAAAAGAT  TAAAAAGGAC  AAAGAACCCA  AGAAGAAGT   TAAGAGCTTC    660

ATGGATCGAA  AGAAGGGATT  TACAGAAGTT  AAGTCGCAGA  ATGGAGAATT  CATGACCCAC    720

AAACTTAAAC  ATACTGAGAA  TACTTTCAGC  CGCCCTGGAG  GGAGGGCCAG  CGTGGACACC    780

AAGGAGGCTG  AGGGCGCCCC  CCAGGTGGAA  GCCGGCAAAA  GGCTGGAGGA  GCTTCGTCGT    840

CGTCGCGGGG  AGACCGAGAG  CGAAGAGTTC  GAGAAGCTCA  ACAGAAGCA   GCAGGAGGCG    900

GCTTTGGAGC  TGGAGGAACT  CAAGAAAAAG  AGGGAGGAGA  GAAGGAAGGT  CCTGGAGGAG    960

GAAGAGCAGA  GGAGGAAGCA  GGAGGAAGCC  GATCGAAAAC  TCAGAGAGGA  GGAAGAGAAG   1020

AGGAGGCTAA  AGGAAGAGAT  TGAAAGGCGA  AGAGCAGAAG  CTGCTGAGAA  ACGCCAGAAG   1080

ATGCCAGAAG  ATGGCTTGTC  AGATGACAAG  AAACCATTCA  AGTGTTTCAC  TCCTAAAGGT   1140

TCATCTCTCA  AGATAGAAGA  GCGAGCAGAA  TTTTTGAATA  AGTCTGTGCA  GAAAAGCAGT   1200

GGTGTCAAAT  CGACCCATCA  AGCAGCAATA  GTCTCCAAGA  TTGACAGCAG  ACTGGAGCAG   1260
```

| | | | | | |
|---|---|---|---|---|---|
| TATACCAGTG | CAATTGAGGG | AACAAAAAGC | GCAAAACCTA | CAAAGCCGGC | AGCCTCGGAT | 1320
| CTTCCTGTTC | CTGCTGAAGG | TGTACGCAAC | ATCAAGAGTA | TGTGGGAGAA | AGGGAATGTG | 1380
| TTTTCATCCC | CCACTGCAGC | AGGCACACCA | AATAAGGAAA | CTGCTGGCTT | GAAGGTAGGG | 1440
| GTTTCTAGCC | GTATCAATGA | ATGGCTAACT | AAAACCCCAG | ATGGAAACAA | GTCACCTGCT | 1500
| CCCAAACCTT | CTGACTTGAG | ACCAGGAGAC | GTATCCAGCA | AGCGGAACCT | CTGGGAAAAG | 1560
| CAATCTGTGG | ATAAGGTCAC | TTCCCCCACT | AAGGTTTGA | | | 1599

( 2 ) INFORMATION FOR SEQ ID NO:12:

( i ) SEQUENCE CHARACTERISTICS:
        ( A ) LENGTH: 1677 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE: Human ( v i i ) IMMEDIATE SOURCE: Hela Cell ( x i ) SEQUENCE DESCRIPTION: SEQ ID NO:12:

| | | | | | |
|---|---|---|---|---|---|
| ATGCTGGGTG | GATCCGGATC | GCATGGAAGA | CGCAGCCTGG | CCGCGCTCTC | CCAAATCGCC | 60
| TACCAGAGGA | ATGACGATGA | TGAAGAGGAG | GCAGCCCGGG | AACGGCGCCG | CCGAGCCCGA | 120
| CAGGAACGGC | TGCGGCAGAA | GCAGGAGGAA | GAATCCTTGG | GACAGGTGAC | CGACCAGGTG | 180
| GAGGTGAATG | CCCAGAACAG | TGTGCCTGAC | GAGGAGGCCA | AGACAACCAC | CACAAACACT | 240
| CAAGTGGAAG | GGGATGATGA | GGCCGCATTC | CTGGAGCGCC | TGGCTCGGCG | TGAGGAAAGA | 300
| CGCCAAAAAC | GCCTTCAGGA | GGCTCTGGAG | CGGCAGAAGG | AGTTCGACCC | AACAATAACA | 360
| GATGCAAGTC | TGTCGCTCCC | AAGCAGAAGA | ATGCAAAATG | ACACAGCAGA | AAATGAAACT | 420
| ACCGAGAAGG | AAGAAAAAAG | TGAAAGTCGC | CAAGAAAGAT | ACGAGATAGA | GGAAACAGAA | 480
| ACAGTCACCA | AGTCCTACCA | GAAGAATGAT | TGGAGGGATG | CTGAAGAAAA | CAAGAAAGAA | 540
| GACAAGGAAA | AGGAGGAGGA | GGAAGAGGAG | AAGCCAAAGC | GAGGGAGCAT | TGGAGAAAAT | 600
| CAGGGAGAAG | AGAAGGGAAC | TAAAGTGCAA | GCTAAAAGAG | AAAAGCTCCA | AGAAGACAAG | 660
| CCTACCTTCA | AAAAGAAGA | GATCAAAGAT | GAAAGATTA | AAAGGACAA | AGAACCCAAA | 720
| GAAGAAGTTA | AGAGCTTCAT | GGATCGAAAG | AAGGGATTTA | CAGAAGTTAA | GTCGCAGAAT | 780
| GGAGAATTCA | TGACCCACAA | ACTTAAACAT | ACTGAGAATA | CTTTCAGCCG | CCCTGGAGGG | 840
| AGGGCCAGCG | TGGACACCAA | GGAGGCTGAG | GGCGCCCCCC | AGGTGGAAGC | CGGCAAAAGG | 900
| CTGGAGGAGC | TTCGTCGTCG | TCGCGGGGAG | ACCGAGAGCG | AAGAGTTCGA | GAAGCTCAAA | 960
| CAGAAGCAGC | AGGAGGCGGC | TTTGGAGCTG | GAGGAACTCA | AGAAAAGAG | GGAGGAGAGA | 1020
| AGGAAGGTCC | TGGAGGAGGA | AGAGCAGAGG | AGGAAGCAGG | AGGAAGCCGA | TCGAAAACTC | 1080
| AGAGAGGAGG | AAGAGAAGAG | GAGGCTAAAG | GAAGAGATTG | AAAGGCGAAG | AGCAGAAGCT | 1140
| GCTGAGAAAC | GCCAGAAGAT | GCCAGAAGAT | GGCTTGTCAG | ATGACAAGAA | ACCATTCAAG | 1200
| TGTTTCACTC | CTAAAGGTTC | ATCTCTCAAG | ATAGAAGAGC | GAGCAGAATT | TTTGAATAAG | 1260
| TCTGTGCAGA | AAAGCAGTGG | TGTCAAATCG | ACCCATCAAG | CAGCAATAGT | CTCCAAGATT | 1320
| GACAGCAGAC | TGGAGCAGTA | TACCAGTGCA | ATTGAGGGAA | CAAAAAGCGC | AAAACCTACA | 1380
| AAGCCGGCAG | CCTCGGATCT | TCCTGTTCCT | GCTGAAGGTG | TACGCAACAT | CAAGAGTATG | 1440
| TGGGAGAAAG | GGAATGTGTT | TTCATCCCCC | ACTGCAGCAG | GCACACCAAA | TAAGGAAACT | 1500
| GCTGGCTTGA | AGGTAGGGGT | TTCTAGCCGT | ATCAATGAAT | GGCTAACTAA | AACCCCAGAT | 1560

```
GGAAACAAGT  CACCTGCTCC  CAAACCTTCT  GACTTGAGAC  CAGGAGACGT  ATCCAGCAAG    1 6 2 0

CGGAACCTCT  GGGAAAAGCA  ATCTGTGGAT  AAGGTCACTT  CCCCCACTAA  GGTTTGA       1 6 7 7
```

( 2 ) INFORMATION FOR SEQ ID NO:13:

( i ) SEQUENCE CHARACTERISTICS:
        ( A ) LENGTH: 2137 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE: Human ( v i i ) IMMEDIATE SOURCE: Hela Cell ( i x ) FEATURE:
        ( A ) NAME/KEY:
        ( B ) LOCATION: 12-1607
        ( C ) IDENTIFICATION METHOD:
        ( D ) OTHER INFORMATION: /note="human caldesmon of lower
            molecular weight"

( i x ) FEATURE:
        ( A ) NAME/KEY:
        ( B ) LOCATION: 2025-2030
        ( C ) IDENTIFICATION METHOD:
        ( D ) OTHER INFORMATION: /note="poly A signal"

( i x ) FEATURE:
        ( A ) NAME/KEY:
        ( B ) LOCATION: 2121-2137
        ( C ) IDENTIFICATION METHOD:
        ( D ) OTHER INFORMATION: /note="poly A site"

( x i ) SEQUENCE DESCRIPTION: SEQ ID NO:13:

```
CAACTGCGGA  CATGCTGGGT  GGATCCGGAT  CGCATGGAAG  ACGCAGCCTG  GCCGCGCTCT      60

CCCAAATCGC  CTACCAGAGG  AATGACGATG  ATGAAGAGGA  GGCAGCCCGG  GAACGGCGCC     120

GCCGAGCCCG  ACAGGAACGG  CTGCGGCAGA  AGCAGGAGGA  AGAATCCTTG  GGACAGGTGA     180

CCGACCAGGT  GGAGGTGAAT  GCCCAGAACA  GTGTGCCTGA  CGAGGAGGCC  AAGACAACCA     240

CCACAAACAC  TCAAGTGGAA  GGGGATGATG  AGGCCGCATT  CCTGGAGCGC  CTGGCTCGGC     300

GTGAGGAAAG  ACGCCAAAAA  CGCCTTCAGG  AGGCTCTGGA  GCGGCAGAAG  GAGTTCGACC     360

CAACAATAAC  AGATGCAAGT  CTGTCGCTCC  CAAGCAGAAG  AATGCAAAAT  GACACAGCAG     420

AAAATGAAAC  TACCGAGAAG  GAAGAAAAAA  GTGAAAGTCG  CCAAGAAAGA  TACGAGATAG     480

AGGAAACAGA  AACAGTCACC  AAGTCCTACC  AGAAGAATGA  TTGGAGGGAT  GCTGAAGAAA     540

ACAAGAAAGA  AGACAAGGAA  AAGGAGGAGG  AGGAAGAGGA  GAAGCCAAAG  CGAGGGAGCA     600

TTGGAGAAAA  TCAGATCAAA  GATGAAAAGA  TTAAAAAGGA  CAAAGAACCC  AAGAAGAAG     660

TTAAGAGCTT  CATGGATCGA  AAGAAGGGAT  TTACAGAAGT  TAAGTCGCAG  AATGGAGAAT     720

TCATGACCCA  CAAACTTAAA  CATACTGAGA  ATACTTTCAG  CCGCCCTGGA  GGGAGGGCCA     780

GCGTGGACAC  CAAGGAGGCT  GAGGGCGCCC  CCCAGGTGGA  AGCCGGCAAA  AGGCTGGAGG     840

AGCTTCGTCG  TCGTCGCGGG  GAGACCGAGA  GCGAAGAGTT  CGAGAAGCTC  AAACAGAAGC     900

AGCAGGAGGC  GGCTTTGGAG  CTGGAGGAAC  TCAAGAAAAA  GAGGGAGGAG  AGAAGGAAGG     960

TCCTGGAGGA  GGAAGAGCAG  AGGAGGAAGC  AGGAGGAAGC  CGATCGAAAA  CTCAGAGAGG    1020

AGGAAGAGAA  GAGGAGGCTA  AAGGAAGAGA  TTGAAAGGCG  AAGAGCAGAA  GCTGCTGAGA    1080

AACGCCAGAA  GATGCCAGAA  GATGGCTTGT  CAGATGACAA  GAAACCATTC  AAGTGTTTCA    1140

CTCCTAAAGG  TTCATCTCTC  AAGATAGAAG  AGCGAGCAGA  ATTTTTGAAT  AAGTCTGTGC    1200
```

-continued

| | | | | | |
|---|---|---|---|---|---|
| AGAAAAGCAG | TGGTGTCAAA | TCGACCCATC | AAGCAGCAAT | AGTCTCCAAG | ATTGACAGCA | 1260
| GACTGGAGCA | GTATACCAGT | GCAATTGAGG | GAACAAAAAG | CGCAAAACCT | ACAAAGCCGG | 1320
| CAGCCTCGGA | TCTTCCTGTT | CCTGCTGAAG | GTGTACGCAA | CATCAAGAGT | ATGTGGGAGA | 1380
| AAGGGAATGT | GTTTTCATCC | CCCACTGCAG | CAGGCACACC | AAATAAGGAA | ACTGCTGGCT | 1440
| TGAAGGTAGG | GGTTTCTAGC | CGTATCAATG | AATGGCTAAC | TAAAACCCCA | GATGGAAACA | 1500
| AGTCACCTGC | TCCCAAACCT | TCTGACTTGA | GACCAGGAGA | CGTATCCAGC | AAGCGGAACC | 1560
| TCTGGGAAAA | GCAATCTGTG | GATAAGGTCA | CTTCCCCCAC | TAAGGTTTGA | GACAGTTCCA | 1620
| GAAAGAACCC | AAGCTCAAGA | CGCAGGACGA | GCTCAGTTGT | AGAGGGCTAA | TTCGCTCTTT | 1680
| TGTATTTATG | TTGATTTACT | AAATTGGGTT | CATTATCTTT | TATTTTCAA | TATCCCAGTA | 1740
| AACCCATGTA | TATTATCACT | ATATTAATA | ATCACAGCTA | GAGATGTTCA | TGGTAAAAGT | 1800
| ACTGCCTTTG | CACAGGAGCC | TGTTTCTAAA | GAAACCCATG | CTGTGAAATA | GAGACTTTTC | 1860
| TACTGATCAT | CATAACTCTG | TATCTGAGCA | GTGATACCAA | CCACATCTGA | AGTCAACAGA | 1920
| AGATCCAAGT | TTAAAATTGC | CTGCGGAATG | TGTGCAGTAT | CTAGAAAAAT | GAACCGTAGT | 1980
| TTTGTTTTTT | TAAATACAGA | AGTCATGTTG | TTTCTGCACT | TTATAATAAA | GCATGGAAGA | 2040
| AATTATCTTA | GTAGGCAATT | GTAACACTTT | TTGAAAGTAA | CCCATTTCAG | ATTTGAAATA | 2100
| CTGCAATAAT | GGTTGTCTTT | AAAAAAAAAA | AAAAAA | | | 2137

( 2 ) INFORMATION FOR SEQ ID NO:14:

( i ) SEQUENCE CHARACTERISTICS:
        ( A ) LENGTH: 2215 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE: Human ( v i i ) IMMEDIATE SOURCE: Hela Cell ( i x ) FEATURE:
        ( A ) NAME/KEY:
        ( B ) LOCATION: 12-1685
        ( C ) IDENTIFICATION METHOD:
        ( D ) OTHER INFORMATION: /note="human caldesmon of higher
            molecular weight"

( i x ) FEATURE:
        ( A ) NAME/KEY:
        ( B ) LOCATION: 2103-2108
        ( C ) IDENTIFICATION METHOD:
        ( D ) OTHER INFORMATION: /note="poly A signal"

( i x ) FEATURE:
        ( A ) NAME/KEY:
        ( B ) LOCATION: 2099-2215
        ( C ) IDENTIFICATION METHOD:
        ( D ) OTHER INFORMATION: /note="poly A site"

( x i ) SEQUENCE DESCRIPTION: SEQ ID NO:14:

| | | | | | |
|---|---|---|---|---|---|
| CAACTGCGGA | CATGCTGGGT | GGATCCGGAT | CGCATGGAAG | ACGCAGCCTG | GCCGCGCTCT | 60
| CCCAAATCGC | CTACCAGAGG | AATGACGATG | ATGAAGAGGA | GGCAGCCCGG | GAACGGCGCC | 120
| GCCGAGCCCG | ACAGGAACGG | CTGCGGCAGA | AGCAGGAGGA | AGAATCCTTG | GGACAGGTGA | 180
| CCGACCAGGT | GGAGGTGAAT | GCCCAGAACA | GTGTGCCTGA | CGAGGAGGCC | AAGACAACCA | 240
| CCACAAACAC | TCAAGTGGAA | GGGGATGATG | AGGCCGCATT | CCTGGAGCGC | CTGGCTCGGC | 300
| GTGAGGAAAG | ACGCCAAAAA | CGCCTTCAGG | AGGCTCTGGA | GCGGCAGAAG | GAGTTCGACC | 360

```
CAACAATAAC AGATGCAAGT CTGTCGCTCC CAAGCAGAAG AATGCAAAAT GACACAGCAG    420

AAAATGAAAC TACCGAGAAG GAAGAAAAAA GTGAAAGTCG CCAAGAAAGA TACGAGATAG    480

AGGAAACAGA AACAGTCACC AAGTCCTACC AGAAGAATGA TTGGAGGGAT GCTGAAGAAA    540

ACAAGAAAGA AGACAAGGAA AAGGAGGAGG AGGAAGAGGA GAAGCCAAAG CGAGGGAGCA    600

TTGGAGAAAA TCAGGGAGAA GAGAAGGGAA CTAAAGTGCA AGCTAAAAGA GAAAAGCTCC    660

AAGAAGACAA GCCTACCTTC AAAAAGAAG AGATCAAAGA TGAAAAGATT AAAAAGGACA    720

AAGAACCCAA AGAAGAAGTT AAGAGCTTCA TGGATCGAAA GAAGGGATTT ACAGAAGTTA    780

AGTCGCAGAA TGGAGAATTC ATGACCCACA AACTTAAACA TACTGAGAAT ACTTTCAGCC    840

GCCCTGGAGG GAGGGCCAGC GTGGACACCA AGGAGGCTGA GGGCGCCCCC CAGGTGGAAG    900

CCGGCAAAAG GCTGGAGGAG CTTCGTCGTC GTCGCGGGGA GACCGAGAGC GAAGAGTTCG    960

AGAAGCTCAA ACAGAAGCAG CAGGAGGCGG CTTTGGAGCT GGAGGAACTC AAGAAAAAGA   1020

GGGAGGAGAG AAGGAAGGTC CTGGAGGAGG AAGAGCAGAG GAGGAAGCAG GAGGAAGCCG   1080

ATCGAAAACT CAGAGAGGAG GAAGAGAAGA GGAGGCTAAA GGAAGAGATT GAAAGGCGAA   1140

GAGCAGAAGC TGCTGAGAAA CGCCAGAAGA TGCCAGAAGA TGGCTTGTCA GATGACAAGA   1200

AACCATTCAA GTGTTTCACT CCTAAAGGTT CATCTCTCAA GATAGAAGAG CGAGCAGAAT   1260

TTTTGAATAA GTCTGTGCAG AAAAGCAGTG GTGTCAAATC GACCCATCAA GCAGCAATAG   1320

TCTCCAAGAT TGACAGCAGA CTGGAGCAGT ATACCAGTGC AATTGAGGGA ACAAAAAGCG   1380

CAAAACCTAC AAAGCCGGCA GCCTCGGATC TTCCTGTTCC TGCTGAAGGT GTACGCAACA   1440

TCAAGAGTAT GTGGGAGAAA GGGAATGTGT TTTCATCCCC CACTGCAGCA GGCACACCAA   1500

ATAAGGAAAC TGCTGGCTTG AAGGTAGGGG TTTCTAGCCG TATCAATGAA TGGCTAACTA   1560

AAACCCCAGA TGGAAACAAG TCACCTGCTC CCAAACCTTC TGACTTGAGA CCAGGAGACG   1620

TATCCAGCAA GCGGAACCTC TGGGAAAAGC AATCTGTGGA TAAGGTCACT TCCCCACTA   1680

AGGTTTGAGA CAGTTCCAGA AAGAACCCAA GCTCAAGACG CAGGACGAGC TCAGTTGTAG   1740

AGGGCTAATT CGCTCTTTTG TATTTATGTT GATTTACTAA ATTGGGTTCA TTATCTTTTA   1800

TTTTTCAATA TCCCAGTAAA CCCATGTATA TTATCACTAT ATTTAATAAT CACAGCTAGA   1860

GATGTTCATG GTAAAAGTAC TGCCTTTGCA CAGGAGCCTG TTTCTAAAGA AACCCATGCT   1920

GTGAAATAGA GACTTTTCTA CTGATCATCA TAACTCTGTA TCTGAGCAGT GATACCAACC   1980

ACATCTGAAG TCAACAGAAG ATCCAAGTTT AAAATTGCCT GCGGAATGTG TGCAGTATCT   2040

AGAAAAATGA ACCGTAGTTT TGTTTTTTA AATACAGAAG TCATGTTGTT TCTGCACTTT    2100

ATAATAAAGC ATGGAAGAAA TTATCTTAGT AGGCAATTGT AACACTTTTT GAAAGTAACC   2160

CATTTCAGAT TTGAAATACT GCAATAATGG TTGTCTTTAA AAAAAAAAA AAAAA         2215
```

( 2 ) INFORMATION FOR SEQ ID NO:15:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: No ( x i ) SEQUENCE DESCRIPTION: SEQ ID NO:15:

```
CAGACCATGG ATCGAAAGAA GGGATTTAC          29
```

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: Yes ( x i ) SEQUENCE DESCRIPTION: SEQ ID NO:16:

TACCGAGCTC AAACCTTAGT GGGGGAAGTG     30

( 2 ) INFORMATION FOR SEQ ID NO:17:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: No ( x i ) SEQUENCE DESCRIPTION: SEQ ID NO:17:

CAGACCATGG CCATCGAGGG TAGGAGACTG GAGCAGTATA CCAGTGC     47

( 2 ) INFORMATION FOR SEQ ID NO:18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: Yes ( x i ) SEQUENCE DESCRIPTION: SEQ ID NO:18:

GCTCGAATTC AAACCTTAGT GGGGGAAGTG     30

( 2 ) INFORMATION FOR SEQ ID NO:19:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: No ( x i ) SEQUENCE DESCRIPTION: SEQ ID NO:19:

CAGACCATGG CCAGACTGGA GCAGTATACC     30

( 2 ) INFORMATION FOR SEQ ID NO:20:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: No ( x i ) SEQUENCE DESCRIPTION: SEQ ID NO:20:

CAGACCATGG CCATCGAGGG TAGGATTGAG GGAACAAAAA GC          42

( 2 ) INFORMATION FOR SEQ ID NO:21:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: Yes ( x i ) SEQUENCE DESCRIPTION: SEQ ID NO:21:

GCTCGAATTC AGGATACGTC TCCTGG          26

( 2 ) INFORMATION FOR SEQ ID NO:22:

( i ) SEQUENCE CHARACTERISTICS:
        ( A ) LENGTH: 94 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Met  Ala  Ile  Glu  Gly  Arg  Ile  Glu  Gly  Thr  Lys  Ser  Ala  Lys  Pro
 1              5                        10                       15

Thr  Lys  Pro  Ala  Ala  Ser  Asp  Leu  Pro  Val  Pro  Ala  Glu  Gly  Val
               20                       25                       30

Arg  Asn  Ile  Lys  Ser  Met  Trp  Glu  Lys  Gly  Asn  Val  Phe  Ser  Ser
                    35                       40                       45

Pro  Thr  Ala  Ala  Gly  Thr  Pro  Asn  Lys  Glu  Thr  Ala  Gly  Leu  Lys
                    50                       55                       60

Val  Gly  Val  Ser  Ser  Arg  Ile  Asn  Glu  Trp  Leu  Thr  Lys  Thr  Pro
                    65                       70                       75

Asp  Gly  Asn  Lys  Ser  Pro  Ala  Pro  Lys  Pro  Ser  Asp  Leu  Arg  Pro
                    80                       85                       90

Gly  Asp  Val  Ser
```

( 2 ) INFORMATION FOR SEQ ID NO:23:

( i ) SEQUENCE CHARACTERISTICS:
        ( A ) LENGTH: 285 base pairs
        ( B ) TYPE: nucleic acid
        ( C ) STRANDEDNESS: double
        ( D ) TOPOLOGY: linear ( i i ) MOLECULE TYPE: cDNA to mRNA ( v i i ) IMMEDIATE SOURCE: Hela Cell ( x i ) SEQUENCE DESCRIPTION: SEQ ID NO:23:

ATGGCCATCG AGGGTAGGAT TGAGGGAACA AAAAGCGCAA AACCTACAAA GCCGGCAGCC          60

TCGGATCTTC CTGTTCCTGC TGAAGGTGTA CGCAACATCA AGAGTATGTG GGAGAAAGGG          120

AATGTGTTTT CATCCCCCAC TGCAGCAGGC ACACCAAATA AGGAAACTGC TGGCTTGAAG          180

GTAGGGGTTT CTAGCCGTAT CAATGAATGG CTAACTAAAA CCCCAGATGG AAACAAGTCA          240

CCTGCTCCCA AACCTTCTGA CTTGAGACCA GGAGACGTAT CCTGA                          285

( 2 ) INFORMATION FOR SEQ ID NO:24:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: No ( x i ) SEQUENCE DESCRIPTION: SEQ ID NO:24:

```
CAGACCATGG CCATTGAGGG AACAAAAAGC          30
```

( 2 ) INFORMATION FOR SEQ ID NO:25:

( i ) SEQUENCE CHARACTERISTICS:
        ( A ) LENGTH: 90 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
Met Ala Ile Glu Gly Thr Lys Ser Ala Lys Pro Thr Lys Pro Ala
  1               5                  10                  15

Ala Ser Asp Leu Pro Val Pro Ala Glu Gly Val Arg Asn Ile Lys
                 20                  25                  30

Ser Met Trp Glu Lys Gly Asn Val Phe Ser Ser Pro Thr Ala Ala
                 35                  40                  45

Gly Thr Pro Asn Lys Glu Thr Ala Gly Leu Lys Val Gly Val Ser
                 50                  55                  60

Ser Arg Ile Asn Glu Trp Leu Thr Lys Thr Pro Asp Gly Asn Lys
                 65                  70                  75

Ser Pro Ala Pro Lys Pro Ser Asp Leu Arg Pro Gly Asp Val Ser
                     80                  85                  90
```

( 2 ) INFORMATION FOR SEQ ID NO:26:

( i ) SEQUENCE CHARACTERISTICS:
        ( A ) LENGTH: 273 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE: Human ( v i i ) IMMEDIATE SOURCE: Hela Cell ( x i ) SEQUENCE DESCRIPTION: SEQ ID NO:26:

```
ATGGCCATTG AGGGAACAAA AAGCGCAAAA CCTACAAAGC CGGCAGCCTC GGATCTTCCT       60
GTTCCTGCTG AAGGTGTACG CAACATCAAG AGTATGTGGG AGAAAGGGAA TGTGTTTTCA      120
TCCCCCACTG CAGCAGGCAC ACCAAATAAG GAAACTGCTG GCTTGAAGGT AGGGGTTTCT      180
AGCCGTATCA ATGAATGGCT AACTAAAACC CCAGATGGAA ACAAGTCACC TGCTCCCAAA      240
CCTTCTGACT TGAGACCAGG AGACGTATCC TGA                                   273
```

( 2 ) INFORMATION FOR SEQ ID NO:27:

( i ) SEQUENCE CHARACTERISTICS:
        ( A ) LENGTH: 88 amino acids (B) TYPE: amino acid
    (C) STRANDEDNESS: single
    (D) TOPOLOGY: linear ( i i ) MOLECULE TYPE: peptide ( x i ) SEQUENCE DESCRIPTION: SEQ ID NO:27:

```
Ile Glu Gly Thr Lys Ser Ala Lys Pro Thr Lys Pro Ala Ala Ser
 1               5                  10                 15

Asp Leu Pro Val Pro Ala Glu Gly Val Arg Asn Ile Lys Ser Met
               20                  25                 30

Trp Glu Lys Gly Asn Val Phe Ser Ser Pro Thr Ala Ala Gly Thr
               35                  40                 45

Pro Asn Lys Glu Thr Ala Gly Leu Lys Val Gly Val Ser Ser Arg
               50                  55                 60

Ile Asn Glu Trp Leu Thr Lys Thr Pro Asp Gly Asn Lys Ser Pro
               65                  70                 75

Ala Pro Lys Pro Ser Asp Leu Arg Pro Gly Asp Val Ser
               80                  85
```

( 2 ) INFORMATION FOR SEQ ID NO:28:

( i ) SEQUENCE CHARACTERISTICS:
    (A) LENGTH: 6 amino acids
    (B) TYPE: amino acid
    (C) STRANDEDNESS: single
    (D) TOPOLOGY: linear ( i i ) MOLECULE TYPE: peptide ( x i ) SEQUENCE DESCRIPTION: SEQ ID NO:28:

```
Met Ala Ile Glu Gly Arg
 1               5
```

( 2 ) INFORMATION FOR SEQ ID NO:29:

( i ) SEQUENCE CHARACTERISTICS:
    (A) LENGTH: 20 base pairs
    (B) TYPE: nucleic acid
    (C) STRANDEDNESS: single
    (D) TOPOLOGY: linear ( i i ) MOLECULE TYPE: other nucleic acid ( i v ) ANTI-SENSE: Yes ( x i ) SEQUENCE DESCRIPTION: SEQ ID NO:29:

CTACAACTGA GCTCGTCCTG          20

( 2 ) INFORMATION FOR SEQ ID NO:30:

( i ) SEQUENCE CHARACTERISTICS:
    (A) LENGTH: 22 base pairs
    (B) TYPE: nucleic acid
    (C) STRANDEDNESS: single
    (D) TOPOLOGY: linear ( i i ) MOLECULE TYPE: other nucleic acid ( i v ) ANTI-SENSE: No ( x i ) SEQUENCE DESCRIPTION: SEQ ID NO:30:

ACATGCTGGG TGGATCCGGA TC       22

( 2 ) INFORMATION FOR SEQ ID NO:31:

( i ) SEQUENCE CHARACTERISTICS:

(A) LENGTH: 20 base pairs
            (B) TYPE: nucleic acid
            (C) STRANDEDNESS: single
            (D) TOPOLOGY: linear (ii) MOLECULE TYPE: other nucleic acid (iv) ANTI-SENSE: Yes (xi) SEQUENCE DESCRIPTION: SEQ ID NO:31:

GGAACTGTCT CAAACCTTAG        20

(2) INFORMATION FOR SEQ ID NO:32:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: other nucleic acid (iv) ANTI-SENSE: Yes (xi) SEQUENCE DESCRIPTION: SEQ ID NO:32:

GTTTAAGTTT GTGGGTCATG AATTCTCC        28

DNA ENCODING A PROTEIN COMPRISING CALMODULIN-AND ACTIN-BINDING HUMAN CALDESMON PEPTIDE FRAGMENT

This is a divisional application of Ser. No. 08/285,440, filed Aug. 4, 1994, now issued as U.S. Pat No. 5,532,337 which is a continuation of now abandoned application Ser. No. 07/858,947, filed Mar. 27, 1992.

BACKGROUND OF THE INVENTION

1. Field of the Invention

This invention relates to a polypeptide that has the amino acid sequence of the functional domain of human caldesmon.

2. Description of Related Art

Caldesmon is a protein that can bind with calmodulin, actin and tropomyosin, found in all tissues except skeletal muscle and cardiac muscle. It contributes to the regulation of actomyosin system in smooth muscle. This regulatory function depends on the concentration of calcium ions (flip-flop regulation) in bringing about the regulation of the actomyosin system (Proc. Natl. Acad. Sci. USA, 78, 5652–5655, 1981). When the concentration of calcium ions is low, caldesmon binds with the actin filament-tropomyosin system, and inhibits the mutual interactions of actin and myosin. When the calcium ion concentration is increased, complexes of active calmodulin and caldesmon are formed. This complex is released from the actin filament-tropomyosin system. Because of this, the inhibition of actin-myosin interaction caused by caldesmon cease, and these interactions begin.

Caldesmon was first isolated from the smooth muscles of chicken gizzards, and it has been isolated from other vertebrates. The results of the limited digestion of chicken caldesmons by the protease α-chymotrypsin have shown that a polypeptide of the size of about 35 kDa at the carboxy-terminal end of chicken caldesmons is the functional unit that brings about flip-flop regulation that depends on the concentration of calcium ions (J. Biochem., 102, 1065–1073, 1987).

There are two isoforms of chicken caldesmon that have different molecular weights. The results of electrophoresis on sodium dodecyl sulfate-polyacrylamide gels have shown that one is of high molecular weight (120,000 to 150,000 Da), now named h-caldesmon, and that the other is of low molecular weight (70,000 to 80,000 Da), now named l-caldesmon. h-caldesmon is abundant in smooth-muscle tissue, and l-caldesmon is abundant in non-muscle tissue and cultured cells. The amino acid sequence of h-caldesmon and the DNA sequence that codes for it have recently been identified (Biochem. Biophys. Res. Commun [called BBRC below], 164, 503–511, 1989), as have been the amino acid sequence of l-caldesmon and the DNA sequence that codes for it (j. Biol. Chem., 266, 355–361, 1991; also Japanese Patent Application 2-37362).

Both h- and l-caldesmons are of chicken origin, and the amino acid sequence of human caldesmon is still unknown.

The morphological change of cells is one characteristic of carcinogenesis. The preservation of cell morphology is closely related to the actin network of the cells, and when cells are transformed, the change in cell morphology occurs in correlation with loss of actin cables, which are part of the filament system that makes up the cytoskeleton (Proc. Natl. Acad. Sci. USA, 72, 994–998, 1975). Immunohistochemical analysis have revealed that caldesmon is localized in actin cables, cell attachment sites, and membrane ruffles in normal cells, but in cancer cells, the compound is not found in any defined cell location (Proc. Natl. Acad. Sci. 81, 3133–3137, 1984).

When cultured cells are transformed with a variety of oncogenic viruses, the caldesmon concentration of the cells decreases and the phosphorylation of the caldesmon increases (Proc. Natl. Acad. Sci. USA 81, 3133–3137, 1984, and Saibo Kogaku [Cell Technology], suppl. 3, "Molecules regulating calcium signalling," 140–153, 1987).

Problems to be solved by this invention

As described above, there seems to be a close relationship between caldesmon content and the change in morphology of cells that have been transformed. If the relationship were understood, it might be possible to use human caldesmon for treatment of cancer. In addition, if the DNA sequence that codes for human caldesmon were known, it would be possible to use it for the diagnosis of cancer. Further, if it were possible to isolate a polypeptide that has activities of the actin-binding functional unit, the tropomyosin-binding functional unit, and the calmodulin-binding unit, this polypeptide could be used to inhibit or accelerate the mutual interactions between actin and myosin whatever the calcium concentration is, so that the polypeptide could be used as a vasodilator or a regulator of the movements of the digestive tract.

The purpose of this invention is to provide a polypeptide that has the activity of human caldesmon and the DNA sequence that codes for said polypeptide.

SUMMARY OF THE INVENTION

To summarize this invention, the first part of this invention relates to a polypeptide that has a calmodulin-binding activity and an actin-binding activity characterized by said polypeptide has an amino acid sequence of SEQ ID NO:1 in the Sequence Listing in a polypeptide molecule. The second part of this invention relates to a gene that codes for the polypeptide of the first part of this invention.

The polypeptide of this invention is a polypeptide that has both calmodulin-binding activity and actin-binding activity; it is, for example, a polypeptide that has within it the amino acid sequence shown as SEQ ID NO:1 in the Sequence Listing, which sequence is that of the functional unit of human caldesmon, which unit was discovered by the inventors of this invention. Polypeptides that have within them this amino acid sequence include, for example, the polypeptides that have the sequence of SEQ ID NO:2 to 5 of the Sequence Listing.

A gene that codes for the polypeptide of artificial human caldesmon is, for example, a gene with the DNA sequence of SEQ ID NO:7 to 12 in the Sequence Listing, and genes that can hybridize under stringent conditions to the gene with the SEQ ID NO:7 to 12, and which genes code for a polypeptide that has calmodulin-binding activity and actin-binding activity.

The inventors of this invention prepared a cDNA library from HeLa cells, a human cell line, and next selected cDNA clones that code for a polypeptide of human caldesmon from this cDNA library; the DNA sequence and the amino acid sequence coded for human caldesmon were deduced by DNA sequence analysis. Next, based on various finding, the inventors prepared polypeptides of various lengths, and looked for the functional domain of human caldesmon polypeptide, using calmodulin-binding activity and actin-binding activity as indices. Based on the findings described below, the inventors achieved this invention.

DETAILED DESCRIPTION OF THE INVENTION

Figure 1:
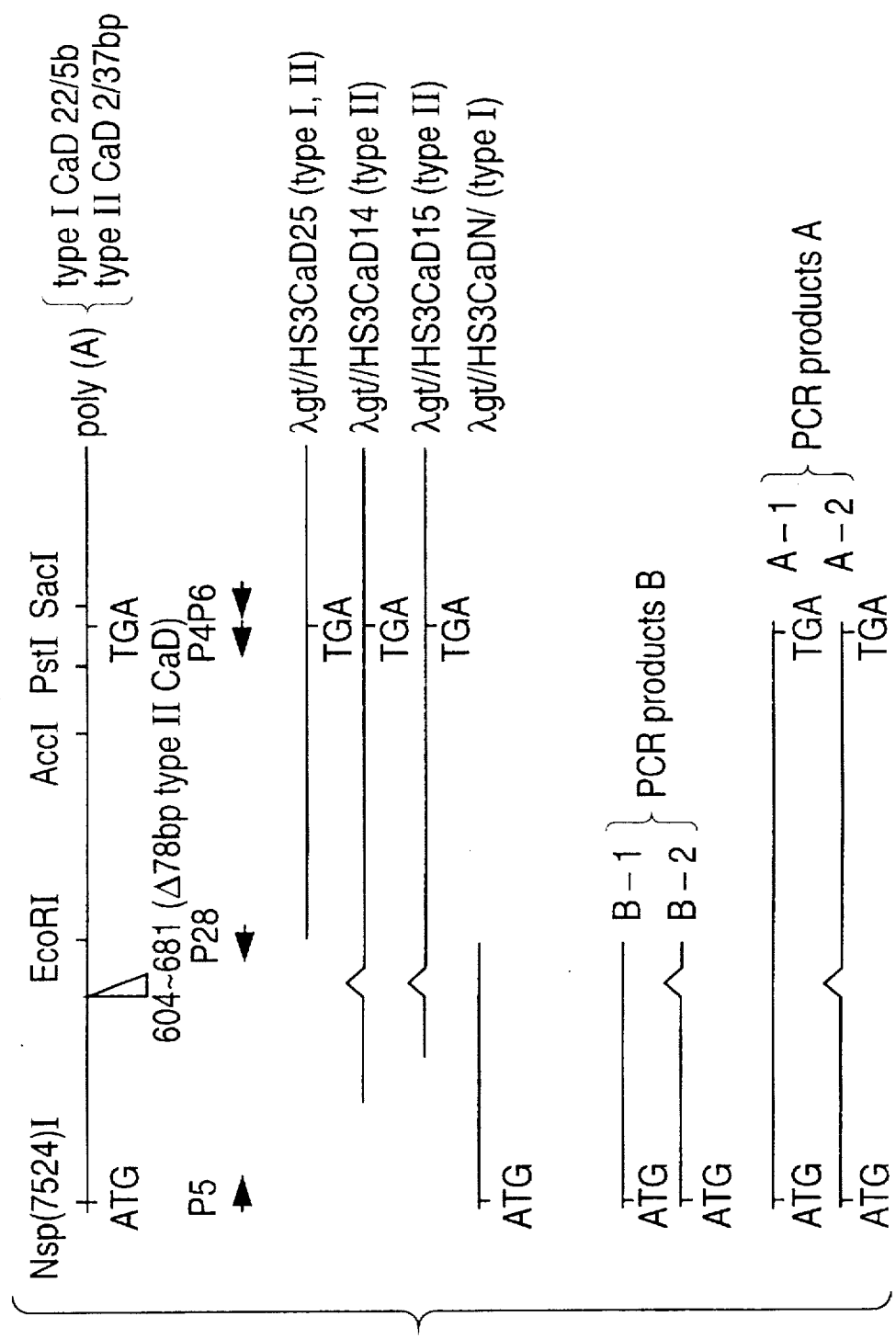
FIG. 1 is a restriction map of the cDNA that codes for type I (SEQ ID NO:6) and type II (SEQ ID NO:5) caldesmon (CaD).

Below, this invention is explained in detail.

The gene that codes for human caldesmon can be isolated and analyzed as described here. To obtain the gene of human caldesmon, HeLa cells or the like can be used, and the total RNA, which includes the poly(A)+ RNA, of the cells, was isolated, and bound onto a cellulose carrier or the like with oligo(dT). This was used as a template in the synthesis of cDNA with reverse transcriptase. The cDNA was synthesized by the method of Okayama-Berg or by the method of Gubler-Hofmann. The cDNA synthesized in this was ligated with a plasmid or phage vector and introduced into a host, giving a cDNA library.

The cDNA library was screened for the desired clones by one of the two following methods. The amino acid sequence of a portion of the desired protein was identified, and an oligonucleotide that coded for that amino acid sequence was synthesized and used as a probe in screening. Or, an antibody that bound with the desired protein was prepared and used to screen the cDNA library constructed in an expression vector, in an immunological method.

When the immunological method of screening is used, λgt11 is well used as the expression vector. λgt11 is commercially available; it can be purchased from, for example, Stratagene. When λgt11 is used in immunological screening, first, the library is amplified on agar plates, and nitrocellulose or nylon filters treated with isopropyl-β-D-galactopyranoside (IPTG) are placed on these plates and expression is induced, after which the protein being expressed adsorbes onto the filter. The filter is immersed in buffer that contains bovine serum albumin (below, referred to as the blocking buffer), and after this step of blocking, antibodies (first antibody) that bind with the desired protein are added to fresh blocking buffer, and the filter is immersed in this blocking buffer, so that the desired protein and the antibodies form complexes. After the filter is washed, it is immersed in a blocking buffer that contains the second antibody, labelled with an enzyme. The first antibody and the second antibody form complexes. Second antibodies coupled to alkaline phosphatase or peroxidase are commercially available. The filter is washed to remove excess second antibody that has not adsorbed to the filter, and the filter is put in a developing solution, and colored clones are selected. The recombinant phages obtained in this way are used to infect host *Escherichia coli* cells, and phage DNA is obtained from the phage lysate. The cDNA from the recombinant phage DNA is isolated and purified, and its DNA sequence is identified.

The antibodies used for immunological screening can be antisera prepared in rabbits immunized with other kinds of caldesmon, such as chicken caldesmon that have amino acid sequences likely to correspond in part to the sequence of the desired protein, human caldesmon.

The cDNA sequence coding for human caldesmon, which has been identified by the inventors, is SEQ ID NO:13 and 14 in the Sequence Listing. Of the two forms of human caldesmon, the 558 amino acid residues shown as SEQ ID NO:6 in the Sequence Listing is that of the caldesmon of high molecular weight, and the DNA sequence that codes for this is SEQ ID NO:12 of the Sequence Listing. The caldesmon of low molecular weight is exactly the same as that of high molecular weight except that it lacks amino acids 202 to 227, and it is shown as the 532 amino acids of SEQ ID NO:5 in the Sequence Listing, and the DNA sequence that codes for this is SEQ ID NO:11 in the Sequence Listing. Here, the form of higher molecular weight is called type I, and the form of lower molecular weight is called type II.

To obtain plasmids that express the polypeptides of human caldesmons type I and type II, DNA that codes for the caldesmon of type I and DNA that codes for the caldesmon of type II are prepared separately from the recombinant phage DNA mentioned above, and the DNA is inserted into an expression plasmid, such as the plasmid pTV118N. The plasmid that coded for the caldesmon of type I was designated pTV118NHS3CaD1, and the plasmid that coded for the caldesmon of type II was designated pTV118NHS3CaD2.

With pTV118NHS3CaD1, it is possible to prepare DNA that codes for polypeptides of various lengths. For example, a site slightly upstream of the initiation codon of the region that codes for type I caldesmon of this plasmid can be cleaved with an appropriate restriction enzyme, and exonuclease can be used to remove the sequence of the 5'-side in the caldesmon gene. By changes in the reaction conditions, it is possible to prepare genes that code for polypeptides of various chain lengths that are missing the N-terminal portion of type I caldesmon. Alternatively, it is possible to amplify DNA of various lengths by the polymerase chain reaction (PCR: Saiki et al., Science, 230, 1350–1354, 1985) with a number of primers synthesized and pTV118NHS3CaD1 as a template, and said DNA can be used to prepare polypeptides of various lengths. As described in detail, with the SEQ ID NO:15 and 16 in the Sequence Listing as primers, PCR can be done (at 94° C. for 30 sec in step 1, at 55° C. for 2 min in step 2, and at 72° C. for 1 min in step 3, for a total of 20 cycles), which results in the amplification of DNA that contains the DNA sequence shown as SEQ ID NO:10 in the Sequence Listing, which codes for the polypeptide shown in the Sequence Listing as having SEQ ID NO:4 (called 312AA below). With the sequences of SEQ ID NO:17 and 18 in the Sequence Listing as primers, it is possible to amplify DNA that contains the DNA sequence shown as SEQ ID NO:9 in the Sequence Listing, which codes for the polypeptide shown in the Sequence Listing as having SEQ ID NO:3 (called 122AA below). With the sequences of SEQ ID NO:18 and 19 in the Sequence Listing as primers, it is possible to amplify DNA that contains the DNA sequence shown as SEQ ID NO:8 in the Sequence Listing, which codes for the polypeptide shown in the Sequence Listing as having SEQ ID NO:2 (called 118AA below). With the SEQ ID NO:20 and 21 in the Sequence Listing as primer, it is possible to amplify DNA that contains the DNA sequence shown as SEQ ID NO:23 in the Sequence Listing, which codes for the polypeptide shown in the Sequence Listing as having SEQ ID NO:22 (called 94AA below). In addition, with the sequences of SEQ ID NO:21 and 24 in the Sequence Listing as primers, it is possible to amplify DNA that contains the DNA sequence shown as SEQ ID NO:26 in the Sequence Listing, which codes for the polypeptide shown in the Sequence Listing as SEQ ID NO:25 (called 90AA below). Next, these DNAs are inserted into expression plasmids, such as, for example, pTV118N. The plasmid that coded for 312AA was named pTHCD247, the plasmid that coded for 122AA was named pTHCDXa443, the plasmid that coded for 118AA was named pTHCD443, the plasmid that coded for 94AA was named pTHCDXa451, and the plasmid that coded for 90AA was named pTHCD451.

The plasmids were used to transform *Escherichia coli* cells, such as *E. coli* JM109, for their expression, and the recombinant cells were cultured under appropriate conditions so that the desired polypeptides accumulated within the *E. coli* cells. The purification of the polypeptides was, for example, as follows. The recombinant *E. coli* cells were cultured in a culture medium such as L broth, and the cells were harvested and disrupted by being sonicated. The disrupted cells were centrifuged and the supernatant was obtained. After treatment such as dialysis, the dialysate was put on a column for gel filtration and then on a column for ion-exchange chromatography for purification. The desired proteins were purified by use of affinity columns coupled with calmodulin or tropomyosin, making use of the properties of the target protein. 122AA and 94AA have a sequence that can be recognized by factor Xa. By cleaving with factor Xa site-specifically, it is possible to prepare a polypeptide shown as SEQ ID NO:1 in the Sequence Listing (called 116AA below) and a polypeptide shown as SEQ ID NO:27 in the Sequence Listing (called 88AA below).

Figure 2:
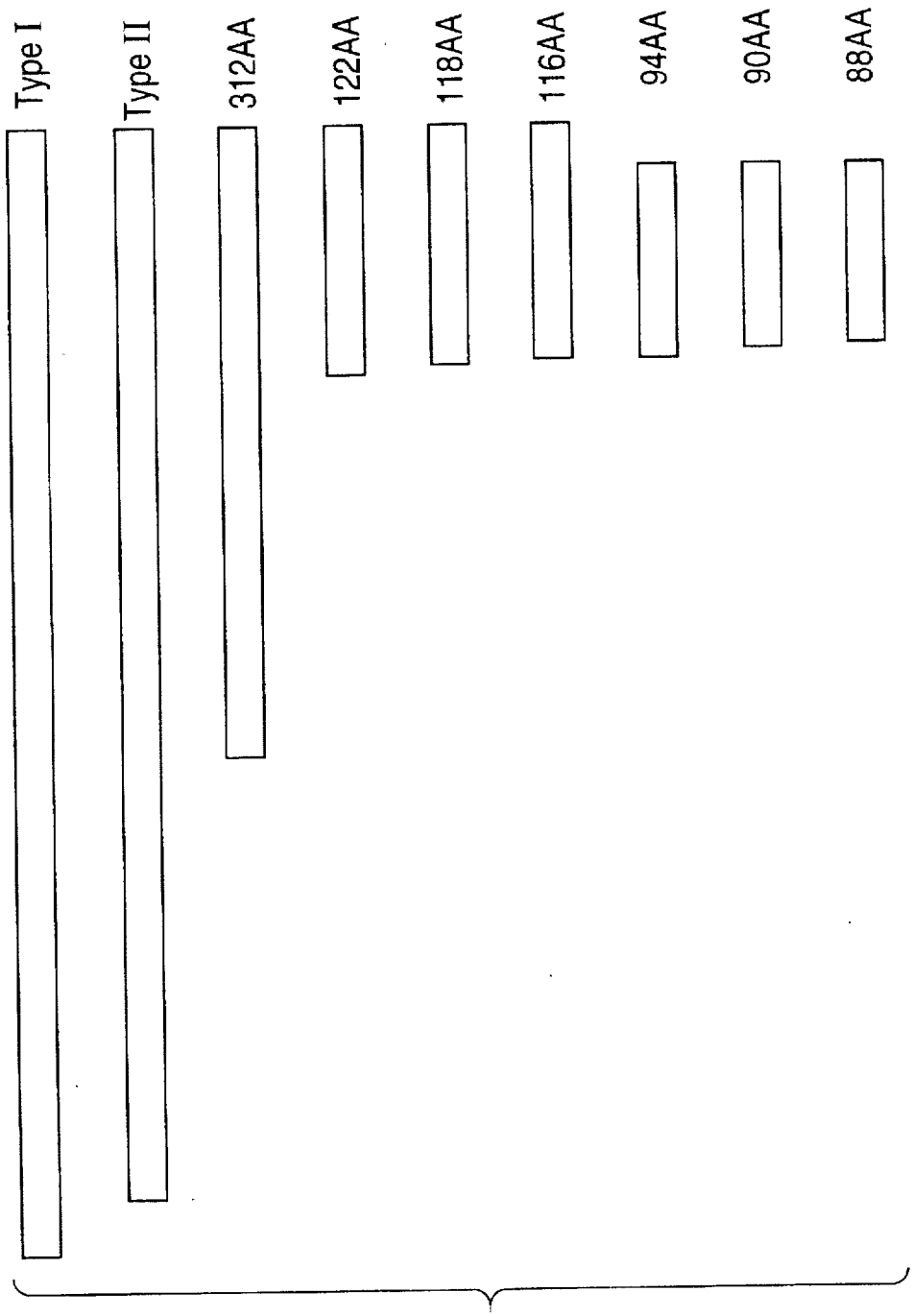
FIG. 2 is a figure that shows the relationships of type I and type II caldesmon, together with the CaD fragments of the present invention comprising SEQ ID NO:1. These CaD fragments are fragments 312AA (SEQ ID NO:3), 118AA (SEQ ID NO:2), 116AA (SEQ ID NO:1), 94AA (SEQ ID NO:22), 90AA (SEQ ID NO:25), and 88AA (SEQ ID NO:27).

The polypeptides to which this invention is related are shown in FIG. 2. Type II is a polypeptide that is missing one portion of type I. 312AA is a polypeptide that is the C-terminal portion of types I and II. 122AA and 118A are polypeptides that have a sequence of 116 amino acids in the C-terminal sequence of 312AA, and 94AA and 90AA are polypeptides that have a sequence of 88 amino acids that are in the central portion of 118AA, lacking both the N-terminal portion and the C-terminal portion. On the N-terminal of 118AA, there are residues Met-Ala that originated from a PCR primer, and on the N-terminal of 90AA, there are residues Met-Ala that also originated from a PCR primer. On the N-terminal of 122AA and 94AA, there are residues Met-Ala that originated from PCR primer and a sequence that can be recognized by factor Xa.

it is possible to measure the calmodulin-binding activity of these polypeptides by use of their affinity for calmodulin during calmodulin-affinity chromatography on a column, and it is possible to measure the actin-binding activity of these polypeptides by the method of coprecipitation with actin. As shown in Table 1, the polypeptide (type I, type II, 312AA, 122AA, 118AA, and 116AA) that contains the polypeptide of 116 amino acids (called 116AA below) that has SEQ ID NO:1 in the Sequence Listing has both calmodulin-binding activity and actin-binding activity.

TABLE 1

| polypeptide | calmodulin-binding activity | actin-binding activity |
| --- | --- | --- |
| type I | + | + |
| type II | + | + |
| 312AA | + | + |
| 122AA | + | + |
| 118AA | + | + |
| 116AA | + | + |
| 94AA | + | − |
| 90AA | + | − |
| 88AA | + | − |

(Activity is shown as +, and lack of activity as −.)

Type I, type II, 312AA, 122AA, 118AA, 116AA all have tropomyosin-binding activity and have a inhibitory activity to actomyosin ATPase, and so the functional unit of human caldesmon is identified as being 116AA.

It is possible to construct a DNA that codes for 116AA out of pTHCD443 as needed by the method of site-specific mutagenesis, and the DNA can be used to express 116AA.

As described above in detail, this invention provides various polypeptides that have activities of human caldesmon and also provides genes that code for these polypeptides. It is possible to produce both on a large scale by the use of genetic engineering, and said genes and polypeptides will be useful in diagnosis and other fields of medicine, and in biochemical research, as well. The functional unit of human caldesmon, 116AA, can be used as a material for chimera proteins and peptide transfer, and the DNA with SEQ ID NO:7 in the sequence listing will be of use in the fields of genetic engineering and protein engineering.

EXAMPLES

Below, this invention will be explained in further detail with reference to examples, but this invention is not to be taken to be limited to these examples.

Example 1

Cloning of cDNA that codes for the polypeptide of human caldesmon from HeLa cells 1-1. Construction of a cDNA library The total RNA of HeLa cells was obtained by the method of guanidium-cesium chloride (Biochemistry, 18, 5294–5299, 1979), and poly(A)$^+$ RNA was isolated by column chromatography with oligo-(dT)cellulose. The purified poly(A)$^+$ RNA was used as a template and oligo-(dT) was used as the primer in the synthesis of cDNA by the method of Gubler-Hoffmann (Gene, 25, 263–269, 1983). The ends of the cDNA were blunted with T4 DNA polymerase, and the EcoRI site in the cDNA was methylated with EcoRI methylase. Next, cDNA was ligated to an EcoRI linker [d(pGGAATTCC)] with use of T4 DNA ligase, and cDNA with both ends having an EcoRI was constructed by EcoRI digestion. This cDNA was ligated with the EcoRI arm of λgt11 (Stratagene), and a cDNA library was made by in vitro packaging with GigapackII Gold (Stratagene).

1-2. Screening of the cDNA library

Plaques of phages with use of *E. coli* Y1090 as the host cells were formed. To do this Y1090 cells were cultured overnight at 37° C., in L medium that contained 0.02% maltose, and the cells were collected by centrifugation. The cells harvested were suspended in 10 mM MgSO$_4$ and were added into a suspension of phage solution and kept at 37° C. for 15 minutes to allow attachment of the phages to the host cells. To this mixture was added a mixture of soft agar (L medium containing 10 mM MgSO$_4$ with agarose added to the final concentration of 0.6%, which medium was autoclaved and then cooled to and kept at 50° C.), and this new mixture was spread on L plates (below, this step is referred to as "plating"). The plates were kept at 42° C. for 3 hours, and after formation of plaques, a nylon membrane (HYBOND-N; Amersham) treated with 100 mM IPTG was placed on the plate and the whole was kept at 37° C. for 3 hours. The nylon membrane was removed from the plate and immunologically screened with rabbit anti-caldesmon antibodies obtained by the immunization of a rabbit with 35 kDa fragment of chicken caldesmon obtained by the digestion with α-chymotrypsin (J. Biochem., 102, 1065–1073, 1987) and with F(ab')$_2$ fragment of goat anti-rabbit immunoglobulin antibody labelled with alkaline phosphatase as the second antibody. Clones that were stained with nitro blue tetrazolium (NBT) and 5-bromo-4-chloro-3-indolylphosphate (BCIP) were positive. Several positive signals were obtained from among the 250,000 clones. The plaques that corresponded to the positive signals were cut out together with agar and suspended in 500 μl of SM solution (50 mM Tris-HCl, 100 mM NaCl, and 10 mM MgSO$_4$, pH 7.5), plated after being diluted appropriately, and screened again as described above, by which procedure it was possible to isolate four phage clones independently.

1-3. Preparation of recombinant λgt11 DNA

Next, $10^5$ of the cloned phages were plated, and the plates were kept first at 42° C. for 3 hours and then at 37° C. overnight. After this, 15 ml of SM solution and a few drops of chloroform were added and the plates were kept at room temperature for 30 minutes. The upper layer of soft agar with the SM solution was removed and put into a centrifuge tube, and centrifuged at 3000 r.p.m for 15 minutes. The supernatant was added 40% (w/v) polyethylene glycol 6000, so that the final concentration of the polyethylene glycol was 10%, and mixed throughly. The mixture was kept at 4° C. for 1 hour and centrifuged at 3000 r.p.m. for 15 minutes. The supernatant was discarded and the precipitate was suspended with SM solution and then left at 4° C. (below, this method is referred to as the plate lysate method). By this procedure, a phage solution with the titer of $1 \times 10^{10}$ pfu/ml was obtained.

E. coli Y1090 cells that had been cultured overnight in L medium were harvested and suspended in 10 mM MgSO$_4$. The cell suspension was mixed with the phage solution mentioned above at multiplicity of infection (moi) of 0.01, and the mixture were left at 37° C. for 15 minutes. The mixture of phages and E. coli cells was used to inoculate L medium that contained 10 mM MgSO$_4$, and continued to be cultured at 37° C. until a considerable amount of bacterial debris remained after lysis. To the culture, sodium chloride was added to the final concentration of 0.5M, chloroform was added to the final concentration of 0.5%, and the mixture was stirred at 37° C. for 15 minutes. The supernatant obtained by centrifugation was mixed with polyethylene glycol 6000 added to the final concentration of 10% (w/v), and the mixture was left overnight at 4° C. The phage precipitate obtained by centrifugation was dissolved in TM solution (50 mM Tris-HCl and 10 mM MgSO$_4$, pH 7.8), and by the method of glycerol step-gradient ultracentrifugation (T. Maniastis et al., Molecular cloning: A laboratory manual, pp. 83–84, Cold Spring Harbor Laboratory, 1982), the phages were purified.

The phages obtained were suspended in TM solution, and DNase I and RNaseA were added to the suspension, which was then kept at 37° C. for 30 minutes before the addition of EDTA, Proteinase K (Sigma), and SDS to the concentrations of 20 mM, 50 μg/ml, and 0.5%, respectively. After then the mixture was kept at 65° C. for 1 hour. Phenol extraction was done, followed by extraction with diethyl ether, and to the aqueous layer, a 1/10 volume of 5M sodium chloride and two volumes of ice-cold ethanol were added, which caused precipitation of the DNA (below, this step is referred to as ethanol precipitation). The mixture was centrifuged and the precipitated DNA was collected, after which it was washed in 70% ethanol and dried before being dissolved in 100 μl of TE solution (10 mM Tris-HCl and 1 mM EDTA, pH 8.0).

1-4. Identification of DNA sequence of the inserted fragment

The recombinant λgt11 DNA prepared as described above was digested with EcoRI, and the inserted fragments were isolated and purified. Then they were cloned at the EcoRI site of M13mp18RF DNA. The recombinant M13mp18RF DNA was digested with SalI and SphI, and by use of exonuclease III (Course in Biochemical Experimentation 1, Methods in genetic research I, pp. 186–200, 1986), a mutant was constructed that lacked various length of sequence at the 5'-side of the SalI end. Another deletion mutant was prepared that was of recombinant M13mp18RF DNA that had the fragment insertion in the opposite orientation. Then E. coli JM109 cells were transformed with each mutant DNA derived from the recombinant M13mp18 and single-stranded DNA was isolated from the M13mp18 derivatives. Its DNA sequence was identified by the dideoxy-mediated chain-termination method, and the amino acid sequence was deduced from the DNA sequence.

Restriction maps of these clones are shown in FIG. 1. The ATG and TGA shown in the FIG. 1 are the initiation codon and the termination codon for translation, respectively.

The results of identification of the DNA sequence suggested that HeLa cells had two kinds of caldesmon. This was checked by use of the PCR. To do this, with primer 6 (shown in FIG. 1 as P6) indicated as SEQ ID NO:29 in the Sequence Listing the first strand of cDNA was synthesized. With both primer 5 (shown in FIG. 1 as P5) indicated as SEQ ID NO:30 of the Sequence Listing and primer 4 (shown in FIG. 1 as P4) indicated as SEQ ID NO:31 in the Sequence Listing as primer 4, the PCR was done, and two kinds of PCR product A (A-1 and A-2) were obtained. Then with primer 5 and primer 28 (shown in FIG. 1 as P28) indicated as SEQ ID NO:32, the PCR was done, and two kinds of PCR product B (B-1 and B-2) were obtained. Restriction maps of PCR products A (A-1 and A-2) and B (B-1 and B-2) are shown in FIG. 1. The DNA sequences of these PCR products were identified by the dideoxy method, and it was confirmed that there were two kinds of caldesmon. The caldesmon of higher molecular weight was composed of the 558 amino acid residues shown as SEQ ID NO:6 in the Sequence Listing, and the caldesmon of lower molecular weight was composed of the 532 amino acid residues shown as SEQ ID NO:5 in the Sequence Listing and was exactly the same as that of higher molecular weight except that it lacked amino acid residues 202 to 227 of the larger caldesmon. The caldesmon of higher molecular weight was named type I, and the caldesmon of lower molecular weight was named type II. The DNA sequence of type I is that shown as SEQ ID NO:12 in the Sequence Listing, and the DNA sequence of type II is that shown as SEQ ID NO:11. Their cDNA sequences are shown as SEQ ID NOS:14 and 13, respectively, in the Sequence Listing.

Example 2

Construction of expression vectors for types I and II 2-1. Construction of a plasmid that coded for type I caldesmon.

A cDNA fragment of about 800 bp that coded for the N-terminal region of type I caldesmon was obtained by EcoRI digestion of λgt11HS3CaDN1, and cloned at the EcoRI site of M13mp18RF DNA, giving M13mp18HS3CaDN1. This M13mp18HS3CaDN1 was digested with Nsp(7524)I, blunt-ended with T4 DNA polymerase, and digested with EcoRI, giving cDNA fragments of about 790 bp. This cDNA fragment was cloned in plasmid pTV118N which was digested with NcoI, treated with Klenow fragment (large fragment of E. coli DNA polymerase I), and digested with EcoRI, giving pTV118NHS3CaDN1.

cDNA fragments about 1.3 kbp long that coded for the C-terminal region of caldesmon were obtained by EcoRI digestion of λgt11HS3CaD25, and cloned at the EcoRI site of M13mp18RF DNA, giving M13mp18HS3CaDC. Then M13mp18HS3CaDC was digested with EcoRI and SacI, giving fragments of cDNA about 940 bp long, which were into pTV118NHS3CaDN1 between the EcoRI and SacI sites, giving plasmid pTV118NHS3CaD1, which coded for type I caldesmon.

Cells of *E. coli* JM109 into which pTV118NHS3CaD1 had been introduced were designated *E. coli* JM109/pTV118NHS3CaD1, and deposited at the Fermentation Research Institute of the Agency of Industrial Science and Technology, Japan, under FERM BP-3673.

2-2. Construction of a plasmid that coded for type II caldesmon

T4 DNA polymerase was used to make blunt ends on PCR product A-2, and the product was cloned at the SmaI site of M13mp18RF DNA so as to be in the same direction in the PCR product A-2 as in the M13mp18 lacZ gene. Then cloned M13mp18PCRA-2 with the plasmid A-2 as an insertion was constructed. M13mp18PCRA-2 was digested with Nsp(7524)I, and after its ends were made blunt with T4 DNA polymerase, it was digested at the multicloning site that originated from M13mp18 with XbaI, and cDNA fragments about 1.6 kbp long were obtained. These were cloned into pTV118N that had been digested with NcoI, treated with Klenow fragment, and then digested with XbaI, giving pTV118NHS3CaD2 PCRA-2. This was digested with EcoRI and HindIII, and ligated with the cDNA fragments about 940 bp long that code for the C-terminal region of the caldesmon obtained by digestion of pTV118NHS3CaD1 with EcoRI and HindIII. The product was designated plasmid pTV118NHS3CaD2, which codes for type II caldesmon.

*E. coli* cells into which pTV118NHS3CaD2 had been introduced were designated *E. coli* JM109/pTV118NHS3CaD2, and deposited at the Fermentation Research Institute of the Agency of Industrial Science and Technology, Japan, under FERM P-12013.

Example 3

Construction of a plasmid that expresses human caldesmon polypeptide 3-1. Construction of a plasmid that codes for 312AA A primer with SEQ ID NO:15 of the Sequence Listing and with the NcoI recognition sequence at its 5'-end and a primer with SEQ ID NO:16 and with the SacI recognition sequence at its 5'-end were synthesized with a DNA synthesizer and purified. Said primers were used together with pTV118NHS3CaD1 as the template in the PCR to amplify DNA that had the DNA sequence shown as SEQ ID NO:10 in the Sequence Listing within its sequence.

Next, this amplification product was digested with NcoI and SacI and extracted with buffered phenol, so that its enzyme activity was lost. For the removal of an excess of dNTP in the PCR reaction mixture, and DNA concentration, the DNA was caused to precipitate with ammonium sulfate and isopropyl alcohol. The precipitated DNA was dissolved with TE solution (10 mM Tris-HCl, pH 8.0, and 1 mM EDTA), and ligated with pTV118N that had been digested with both NcoI and SacI, giving the plasmid pTHCD247, which codes for 312AA.

*E. coli* JM109 cells into which pTHCD247 had been introduced were designated *E. coli* JM109/pTHCD247, and deposited at the Fermentation Research Institute of the Agency of Industrial Science and Technology, Japan, under FERM BP-3671.

3-2. Construction of a plasmid that codes for 118AA

A primer with SEQ ID NO:19 of the Sequence Listing and with the NcoI recognition sequence at its 5'-end and a primer with SEQ ID NO:18 and with the EcoRI recognition sequence at its 5'-end were synthesized with a DNA synthesizer and purified. Said primers were used together with pTV118NHS3CaD1 as the template in the PCR to amplify DNA that had the DNA sequence shown as SEQ ID NO:8 in the Sequence Listing within its sequence.

Next, this amplification product was digested with NcoI and EcoRI, and treated as in section 3-1 above before being ligated with pTV118N that had been digested with both NcoI and EcoRI, giving the plasmid pTHCD443, which codes for 118AA.

*E. coli* JM109 cells into which pTHCD443 had been introduced were designated *E. coli* JM109/pTHCD443, and deposited at the Fermentation Research Institute of the Agency of Industrial Science and Technology, Japan, under FERM BP-3672.

3-3. Construction of a plasmid that codes for 122AA

A primer with SEQ ID NO:17 of the Sequence Listing and with the NcoI recognition sequence and the factor Xa recognition sequence at its 5'-end was synthesized with a DNA synthesizer and purified. Next, said primer and the primer described above as having SEQ ID NO:18 were used together with pTV118NHS3CaD1 as the template in the PCR to amplify DNA that had the DNA sequence shown as SEQ ID NO:9 in the Sequence Listing within its sequence.

Next, this amplification product was digested with NcoI and EcoRI, and ligated with pTV118N, which had also been digested both NcoI and EcoRI, giving a plasmid that coded for 122AA. Said plasmid was designated pTHCDXa443, and cells of *E. coli* JM109 into which the plasmid was introduced were named *E. coli* JM109/pTHCDXa443.

3-4. Construction of a plasmid that codes for 90AA

A primer with SEQ ID NO:24 of the Sequence Listing and with the NcoI recognition sequence at its 5'-end and a primer with SEQ ID NO:21 and the EcoRI recognition sequence at its 5'-end were synthesized with a DNA synthesizer and purified. Said primers were used together with pTV118NHS3CaD1 as the template in the PCR to amplify DNA that had the DNA sequence shown as SEQ ID NO:26 in the Sequence Listing within it. Next, this amplification product was digested with NcoI and EcoRI, and ligated with pTV118N that had been digested with NcoI and EcoRI, giving the plasmid pTHCD451, which codes for 90AA.

*E. coli* JM109 cells into which pTHCD451 had been introduced were designated *E. coli* JM109/pTHCD451.

3-5. Construction of a plasmid that codes for 94AA

A primer with SEQ ID NO:20 of the Sequence Listing and with the NcoI recognition sequence and the factor Xa recognition sequence at its 5'-end was synthesized with a DNA synthesizer and purified. Said primer and the primer described above as having SEQ ID NO:21 were used together with pTV118NHS3CaD1 as the template in the PCR to amplify DNA that had the DNA sequence shown as SEQ ID NO:23 in the Sequence Listing within its sequence.

Next, this amplification product was digested with NcoI and EcoRI and ligated with pTV118N, which had also been digested both NcoI and EcoRI, giving a plasmid that coded for 94AA. Said plasmid was designated pTHCDXa451, and cells of *E. coli* JM109 into which the plasmid was introduced were named *E. coli* JM109/pTHCDXa451.

Example 4

Expression of human caldesmon polypeptide in *E. coli*

4-1. Expression of type I in *E. coli*

Cells of *E. coli* JM109 which carried pTV118NHS3CaD1 (FERM BP-3673) were used to inoculate 5 ml of L medium that contained 50 µg/ml ampicillin, and the culture was incubated with shaking overnight at 37° C. This seed culture was used to inoculate 500 ml of L medium with the same concentration of ampicillin, and the culture was incubated with shaking overnight at 37° C. When the cells reached the mid-logarithmic stage of growth, IPTG was added to the final concentration of 2 mM, and culture was continued for 17 hours more before the cells were harvested.

The cells were suspended in E solution (0.3M KCl, 0.5 mM EGTA, 0.5 mM $MgCl_2$, 0.5 mM dithiothreitol (DTT), 0.3 mM PMSF, and 50 mM Tris-HCl, pH 7.0), and the suspension was sonicated to disrupt the cells. The suspension was centrifuged and the supernatant was incubated at 95° C. for 5 minutes and then cooled. This was centrifuged and the precipitate was removed. The supernatant was dialyzed against C1 solution (120 mM NaCl, 0.1 mM EGTA, 0.2 mM DTT, and 10 mM Tris-HCl, pH 7.3). The inner solution during dialysis was passed through a column of DEAE Toyopearl 650M equilibrated with C1 solution. To the pass-through fraction, calcium chloride was added to the final concentration of 5 mM, the mixture was passed through a column of Sepharose 4B (Pharmacia LKB) coupled with calmodulin which equilibrated with C2 solution (70 mM NaCl, 0.2 mM $CaCl_2$, 0.1 mM DTT, and 10 mM Tris-HCl, pH 7.5) as described elsewhere (Journal of Biochemistry, 102, 1065–1073, 1987), and type I purified was extracted with C2 solution that contained 1.2 mM EGTA and purified.

4-2. Expression of type II in *E. coli*

Cells of *E. coli* JM109 which carried pTV118NHS3CaD2 (FERM P-12013) were cultured under the same conditions as in the example of 4-1 above, extracted, heated, put on a column of resin for affinity chromatography with calmodulin, and purified, giving type II.

4-3. Expression of 312AA, 122AA, 118AA, 94AA, and 90AA in *E. coli*

Cells of *E. coli* JM109/pTHCD247 (FERM BP-3671), of *E. coli* JM109/pTHCDXa443, of *E. coli* JM109/pTHCD443 (FERM BP-3672), of *E. coli* JM109/pTHCDXa451 and of *E. coli* JM109/pTHCD451 were cultured under the same conditions as in the example of 4-1 above, and purification gave 312AA, 122AA, 118AA, 94AA, and 90AA.

4-4. Preparation of 116AA and 88AA

122AA and 94AA were treated with restriction proteinase factor Xa (Takara Shuzo Co., Ltd.) for 5 hours at 37° C., and a column of calmodulin-Sepharose was used to purify 116AA and 88AA from the digest.

Example 5

Assay of physiological activity 5-1. Assay of calmodulin-binding activity and actin-binding activity For the assay of calmodulin-binding activity, polypeptides purified as described above were mixed with 10 volumes of CaB buffer (10 mM Tris-HCl, pH 7.5, 100 mM KCl, 0.1 mM DTT, and 0.2 mM $CaCl_2$), and put on a column of Sepharose 4B (Pharmacia) coupled with calmodulin which equilibrated with the same buffer. This allowed binding of the polypeptide with calmodulin. After the column was washed with a large amount of the same buffer, the bound polypeptide was eluted from the column with the same buffer, except that 1 mM EGTA was added to the buffer instead of $CaCl_2$. A portion of each fraction was put on an SDS-polyacrylamide gel and electrophoresed, and the presence of the polypeptide in question was confirmed. For the assay of actin-binding activity, the co-precipitation method (BBRC, 132, 645–651, 1985, and Journal of Biochemistry, 102, 1065–1073, 1987) was used.

To 100 µl of a 2 mg/ml solution of monomeric actin prepared by the Staub method (Journal of Biological Chemistry, 188, 559 (1959)), 20 µl of 10 mM ATP, 40 µl of 5× buffer (50 mM Tris-HCl, pH 7.5, 500 mM KCl, 1 mM $CaCl_2$, and 0.5 mM DTT), 20 µl purified polypeptide, and water were added for a total volume of 196 µl, and then 4 µl of 100 mM $MgCl_2$ was added. The mixture was left at room temperature for 1 hour. By the addition of $MgCl_2$, the monomeric actin was polymerized and became filamentous actin. After the polymerization, the mixture was centrifuged at 200,000×g for 30 minutes. The monomeric actin remained in the supernatant, whereas the filamentous actin and proteins bound with it (the polypeptide of this invention) precipitated together. The supernatant and the precipitate were separately electrophoresed on SDS-polyacrylamide gels, and the binding of the polypeptide with actin was confirmed.

The results shown in the Table 1 above, were that the polypeptide that contained 116AA in its sequence had both kinds of activity.

5-2. Assay of tropomyosin-binding activity and inhibition of actomyosin ATPase activity The ability of type I, type II, 312AA, 122AA, 118AA, and 116AA which have the activities described in 5-1, to bind with tropomyosin and to inhibit actomyosin ATPase activity was measured.

For the assay of tropomyosin-binding activity, an affinity column with tropomyosin was prepared by the coupling of tropomyosin with Sepharose 4B (Pharmacia) activated with CNBr. The column was equilibrated with TMB buffer (10 mM Tris-HCl, pH 7.0, 2 mM $MgCl_2$, and 0.5 mM DTT), and a solution of a purified polypeptide diluted, 10 times in the same buffer was put on the column to allow binding of the polypeptide to the column. The column was washed thoroughly with the same buffer, and after substances that had bound nonspecifically were removed in this way, elution was done with slowly increasing concentrations of potassium chloride. A portion of each fraction was put on an SDS-polyacrylamide gel and electrophoresed, and the polypeptide in question was found in the fractions that had been eluted with potassium chloride at the concentrations of 40 to 60 mM.

For the assay of the inhibition of actomyosin-ATPase by the polypeptide of this invention, first, phosphorylated myosin (final concentration, 0.2 mg/ml), actin (final concentration, 0.1 mg/ml), and tropomyosin (final concentration, 30 µg/ml) were added to a buffer that contained 20 mM imidazole-HCl (pH 7.2), 0.1 mM DTT, 100 mM KCl, 2 mM $MgCl_2$, 1 mM ATP, and 0.1 mM $CaCl_2$. Then the purified polypeptide was added and the mixture was kept at 30° C. for 5 minutes. After this reaction time, trichloroacetic acid was added to the final concentration of 10% to stop the reaction. The reaction mixture was centrifuged, and the amount of free phosphate in the supernatant was assayed by the method of Youngburg (BBRC, 132, 645–651, 1985). The inhibition caused by the polypeptide was found from the difference in the amount of free phosphate related by ATPase in the presence and absence of the polypeptide. Both of these activities were found in type I, type II, 312AA, 122AA, 118AA, and 116AA. The functional unit of human caldesmon polypeptide was found to be 116AA.

Results of the invention

As shown by the results described above, this invention provides the complete amino acid sequence of human caldesmon, and the complete DNA sequence that codes for human caldesmon, and it identifies the functional unit of caldesmon activity. These genes and the polypeptides are useful in the fields of biochemistry, medicine, including diagnosis, and the like.

What we claim is:

1. An isolated DNA encoding an actin- or calmodulin-binding polypeptide fragment of a human caldesmon protein, said DNA comprising a nucleotide sequence encoding at least the amino acid sequence shown in SEQ ID NO:1, wherein said caldesmon protein has the amino acid sequence shown in SEQ ID NO:5 or SEQ ID NO:6.

2. The DNA according to claim 1, comprising a nucleotide sequence encoding the amino acid sequence shown in SEQ ID NO:2, SEQ ID NO:3 or SEQ ID NO:4.

3. The DNA according to claim 1, which comprises the nucleotide sequence shown in SEQ ID NO:7.

4. The DNA according to claim 1, which comprises a nucleotide sequence selected from the group consisting of SEQ ID NO:7, SEQ ID NO:8, SEQ ID NO:9 and SEQ ID NO:10.

5. An isolated DNA which is complementary to the DNA according to any one of claims 1, 2, 3, or 4.

6. An isolated DNA which hybridizes under stringent conditions with the complement of the DNA according to any one of claims 1, 2, 3 or 4, said DNA coding for a human polypeptide that has calmodulin-binding activity and actin-binding activity.

7. An isolated DNA encoding a chimeric protein, comprising the DNA according to any one of claims 1, 2, 3, or 4.

8. A cDNA which codes for a human caldesmon protein having the amino acid sequence shown in SEQ ID NO:5 or SEQ ID NO:6.

9. The cDNA according to claim 8, which has a nucleotide sequence shown in SEQ ID NO:11, SEQ ID NO:12, SEQ ID NO:13 or SEQ ID NO:14.

10. A recombinant vector comprising the DNA according to any one of claims 1, 2, 3, 4 or 7 or the cDNA according to any one of claims 8 or 9.

11. A host cell transformed with the recombinant vector according to claim 10.

12. A process for producing a human caldesmon protein or active fragment thereof, which comprises:

culturing the host cell according to claim 11 under conditions to express the human caldesmon protein or active fragment thereof, and isolating the caldesmon protein or active fragment.

* * * * *